US010096386B2

(12) United States Patent
Grill et al.

(10) Patent No.: US 10,096,386 B2
(45) Date of Patent: Oct. 9, 2018

(54) SYSTEMS AND METHODS FOR MODEL-BASED OPTIMIZATION OF SPINAL CORD STIMULATION ELECTRODES AND DEVICES

(71) Applicant: Duke University, Durham, NC (US)

(72) Inventors: Warren M. Grill, Durham, NC (US); Bryan Howell, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 15/321,801

(22) PCT Filed: Jul. 1, 2015

(86) PCT No.: PCT/US2015/038735
§ 371 (c)(1),
(2) Date: Dec. 23, 2016

(87) PCT Pub. No.: WO2016/004152
PCT Pub. Date: Jan. 7, 2016

(65) Prior Publication Data
US 2017/0161454 A1 Jun. 8, 2017

Related U.S. Application Data

(60) Provisional application No. 62/020,479, filed on Jul. 3, 2014.

(51) Int. Cl.
*G06F 19/00* (2018.01)
*G16H 50/50* (2018.01)
(Continued)

(52) U.S. Cl.
CPC .......... *G16H 50/50* (2018.01); *A61N 1/0551* (2013.01); *A61N 1/36185* (2013.01);
(Continued)

(58) Field of Classification Search
CPC .............. A61N 1/36114; A61N 1/0529; A61N 1/0551; A61N 1/36053; G06F 19/3481
See application file for complete search history.

(56) References Cited

U.S. PATENT DOCUMENTS 5,501,703 A 3/1996 Holsheimer et al.
9,656,074 B2 * 5/2017 Simon ................ A61N 1/36053
(Continued)

FOREIGN PATENT DOCUMENTS

JP 2012-504458 A 2/2012
WO 2006019764 A2 2/2006
(Continued)

OTHER PUBLICATIONS

International Search Report and Written Opinion for PCT/US2015/038735 dated Oct. 7, 2015.
(Continued)

*Primary Examiner* — Nicholas Tobergte
(74) *Attorney, Agent, or Firm* — Olive Law Group, PLLC

(57) ABSTRACT

Systems and methods for model-based optimization of spinal cord stimulation electrodes and devices are disclosed. According to an aspect a method includes providing a patient-specific electroanatomical model including the spine, spinal cord, and a map of target neural elements and non-target neural elements. The method also includes using model electrodes to stimulate the target neural elements. Further, the method includes determining differences in activation thresholds between the target neural elements and the non-target neural elements in a plurality of different configurations of the model electrodes. The method also includes generating an optimal spinal cord stimulation electrode configuration based on the determined differences in activation thresholds.

29 Claims, 19 Drawing Sheets

(51) Int. Cl.
- *G06F 17/13* (2006.01)
- *A61N 1/05* (2006.01)
- *A61N 1/36* (2006.01)
- *A61N 1/372* (2006.01)

(52) U.S. Cl.
CPC ......... *A61N 1/37241* (2013.01); *G06F 17/13* (2013.01); *G06F 19/3437* (2013.01)

(56) References Cited

U.S. PATENT DOCUMENTS

| | | |
|---|---|---|
| 2004/0116978 A1 | 6/2004 | Bradley |
| 2006/0149337 A1 | 7/2006 | John |
| 2007/0191895 A1* | 8/2007 | Foreman ............ A61N 1/36114 607/14 |
| 2008/0004674 A1* | 1/2008 | King .................. A61N 1/0529 607/46 |
| 2008/0215119 A1* | 9/2008 | Woods ................ A61N 1/0551 607/59 |
| 2009/0287271 A1 | 11/2009 | Blum et al. |
| 2010/0191307 A1 | 7/2010 | Fang et al. |
| 2011/0040351 A1* | 2/2011 | Butson ............... G06F 19/3481 607/59 |
| 2012/0172946 A1 | 7/2012 | Alataris et al. |
| 2013/0150922 A1 | 6/2013 | Butson et al. |
| 2014/0163640 A1 | 6/2014 | Edgerton et al. |
| 2014/0180361 A1 | 6/2014 | Burdick et al. |
| 2015/0202446 A1 | 7/2015 | Franke et al. |

FOREIGN PATENT DOCUMENTS

| | | |
|---|---|---|
| WO | 2009061813 A1 | 5/2009 |
| WO | 2010/065888 A2 | 6/2010 |

OTHER PUBLICATIONS

International Preliminary Report on Patentability for PCT/US2015/038735 dated Jan. 3, 2017.
European Search Report and Opinion for European Patent Application No. 15814864.3 dated Jan. 8, 2018.
Office Action for Japanese Patent Application No. JP 2016-501841 dated Jan. 9, 2018.
Office Action issued in counterpart Japanese Patent Application No. JP 2016-501846 dated Feb. 27, 2018.
Non-Final Office Action issued in counterpart U.S. Appl. No. 14/774,160 dated Apr. 6, 2018.
Final Office Action issued in counterpart U.S. Appl. No. 14/774,156 dated May 7, 2018.
Notice of Acceptance issued in counterpart Australian Application No. 2014244386 dated May 11, 2018 (three (3) pages).
Second Office Action issued in counterpart Japanese Application No. 2016-501841 dated May 15, 2018 with English translation (eighteen (18) pages).
Australian Examination Report issued in counterpart Australian Application No. 2014244318 dated May 20, 2018, (three (3) pages).

* cited by examiner

SYSTEMS AND METHODS FOR MODEL-BASED OPTIMIZATION OF SPINAL CORD STIMULATION ELECTRODES AND DEVICES

CROSS REFERENCE TO RELATED APPLICATION

This is a 371 national stage patent application which claims priority to PCT International Patent Application No. PCT/US2015/038735, filed Jul. 1, 2015 and titled SYSTEMS AND METHODS FOR MODEL-BASED OPTIMIZATION OF SPINAL CORD SIMULATION ELECTRODES, which claims priority to U.S. Provisional Patent Application No. 62/020,479, filed Jul. 3, 2014 and titled SYSTEMS AND METHODS FOR MODEL-BASED OPTIMIZATION OF SPINAL CORD STIMULATION ELECTRODES, the entire content of which is incorporated herein by reference in its entirety.

TECHNICAL FIELD

The presently disclosed subject matter relates to biomedical systems and devices. Particularly, the presently disclosed subject matter relates to systems and methods for model-based optimization of spinal cord stimulation electrodes.

BACKGROUND

Spinal cord stimulation (SCS) has emerged as a promising therapy for treating chronic, intractable pain in individuals refractory to kinetic (e.g., rehabilitation), pharmaceutical, and surgical therapies. For example, across 74 studies looking at 3,025 individuals with chronic leg and back pain, 58% of the patients reported greater than 50% reduction in pain following SCS. However, despite its success, current SCS devices are still prone to failures; the three most common being poor pain coverage, lead migration, and lead breakage. Poor pain coverage and small lead misplacements can sometimes be overcome by reprogramming the stimulation parameters, but large lead misplacements and lead breakage require an additional surgery to reposition or replace the lead. These revision surgeries are costly, as they add additional expenses (e.g., time off work and additional stimulator hardware), and they obligate the patient to incur risks associated with the surgery. Therefore, there are still opportunities for improving SCS, such as lead design.

Typical SCS devices include an implantable pulse generator (IPG) placed subcutaneously in the buttock or abdomen and a set of wires connecting the IPG to an array of stimulation electrodes placed in the epidural space of the spinal canal. Currently, there are two types of array designs: percutaneous arrays of 4-8 cylindrical electrodes on a cylindrical substrate and surgical (i.e., paddle) arrays of 4-20 rectangular/disk electrodes on a planar substrate, both of which are implanted parallel to the long axis of the spine. Arrays are advantageous because each contact can be programmed individually, making outcomes less sensitive to anatomical variations and differences in electrode placement, but with increasing number of electrodes, programming becomes a challenge.

Computational modelling can be useful tool for SCS device design. Modeling studies have shown that percutaneous arrays in longitudinal (rostral-caudal) bipolar and tripolar configurations, and paddle arrays in transverse (medial-lateral) tripolar configurations, outperform monopolar configurations in selective activation of the targets of SCS, the dorsal column (DC) fibers, over the undesirable targets, the dorsal root (DR) fibers. However, other than a couple of studies looking at optimal electrode geometry and spacing for a longitudinal bipolar and tripolar configuration; lead design, lead placement, and selection of stimulation parameters has been largely a trial and error process. Trial and error experimentation is not an efficient approach and is unlikely to lead to an optimal result, as the efficacy of SCS depends on the geometry, polarity, and location of the stimulation electrodes. Although there have been advances in SCS, there is a continuing need for improved techniques and systems for optimizing SCS.

SUMMARY

Systems and methods for model-based optimization of spinal cord stimulation electrodes and devices are disclosed. According to an aspect a method includes providing a patient-specific electroanatomical model including the spine, spinal cord, and a map of target neural elements and non-target neural elements. The method also includes using model electrodes to stimulate the target neural elements. Further, the method includes determining differences in activation thresholds between the target neural elements and the non-target neural elements in a plurality of different configurations of the model electrodes. The method also includes generating an optimal spinal cord stimulation electrode configuration based on the determined differences in activation thresholds.

It is to be understood that both the foregoing general description and the following detailed description present embodiments, and are intended to provide an overview or framework for understanding the nature and character of the disclosure. The accompanying drawings are included to provide a further understanding, and are incorporated into and constitute a part of this specification. The drawings illustrate various embodiments, and together with the description serve to explain the principles and operation of the concepts disclosed.

BRIEF DESCRIPTION OF THE SEVERAL VIEWS OF THE DRAWINGS

The foregoing aspects and other features of the present subject matter are explained in the following description, taken in connection with the accompanying drawings, wherein.

DETAILED DESCRIPTION

For the purposes of promoting an understanding of the principles of the present disclosure, reference will now be made to various embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one [i.e. at least one) of the grammatical object of the article. By way of example, "an element" means at least one element and can include more than one element. Unless otherwise defined, all technical terms used herein have the same meaning as commonly understood by one of ordinary skill in the art to which this disclosure belongs.

Systems and methods in accordance with embodiments of the present disclosure utilize model-based optimization techniques for developing improved SCS devices. In accordance with embodiments, numerical algorithms (genetic algorithms) are utilized to optimize lead designs for increasing the selectivity of SCS in activating targeted neural elements over non-targeted neural elements. The targeted neural elements are the dorsal column (DC) fibers or axons. The non-targeted neural elements are the dorsal root (DR) fibers or axons. Initial computational modeling work indicates that placement of the stimulation array in the intradural space of the spinal canal allows for better selective activation of DC fibers over DR fibers using markedly (less than 90%) less power, compared to epidural electrodes. Further, an azimuthal array of electrodes in a tripolar configuration had improved selectivity of activation of DC fibers over DR fibers as compared to longitudinal and transverse tripolar configurations used clinically. Together, these results suggest that intradural placement of novel electrode designs can be used to increase the efficiency and efficacy of SCS. Efficiency refers to the energy required to activate the targeted neural elements. Efficacy refers to the ability to activate selectively the targeted DC fibers, which produces pain relief, while minimizing activation of the non-targeted DR fibers, which produces uncomfortable side effects.

Reference will now be made in detail to the embodiments, examples of which are illustrated in the accompanying drawings, in which some, but not all embodiments are shown. Indeed, the concepts may be embodied in many different forms and should not be construed as limiting herein; rather, these embodiments are provided so that this disclosure will satisfy applicable legal requirements. Whenever possible, like reference numbers will be used to refer to like components or parts.

Figure 1:
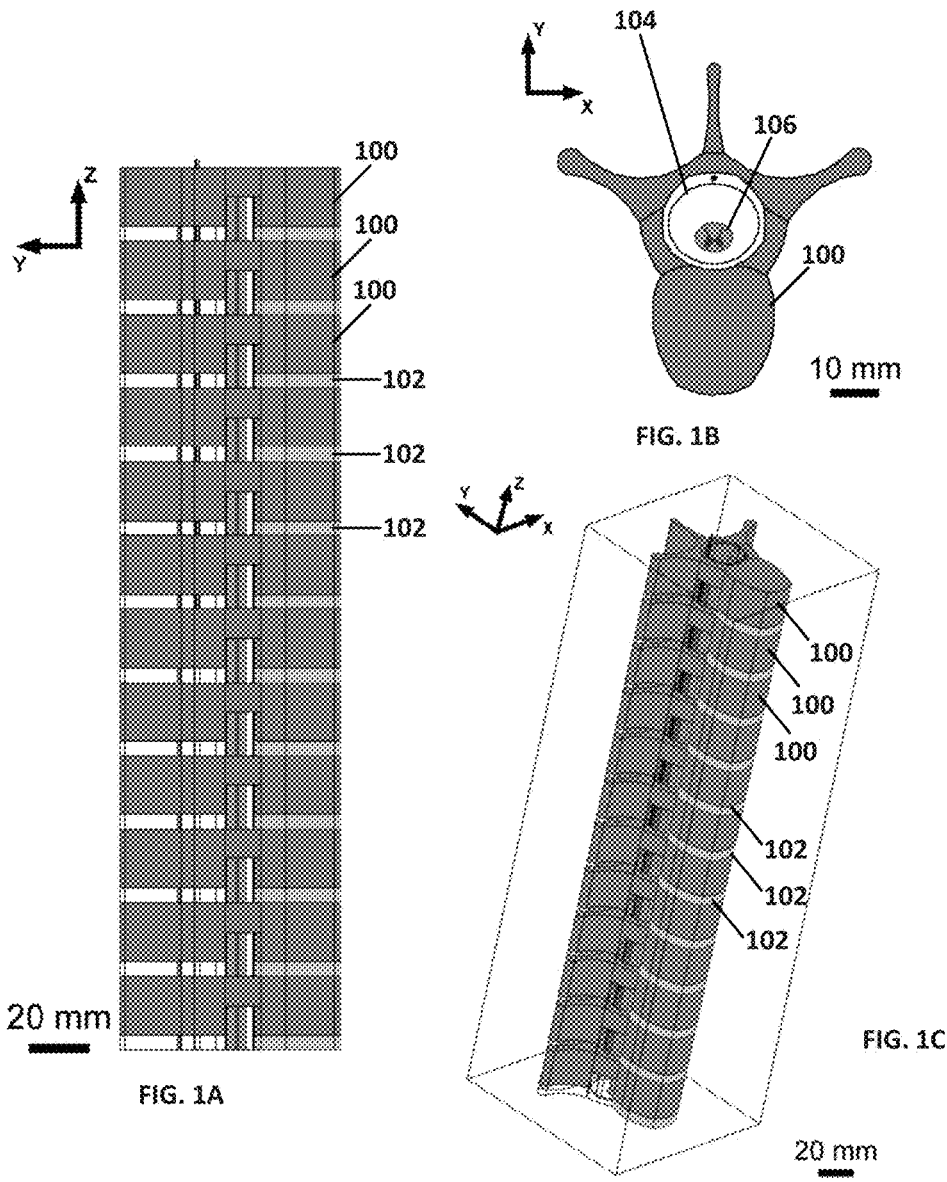
FIGS. 1A-1C are different views of an example finite element model of a spine and spinal cord in accordance with embodiments of the present disclosure.
Figure 2:
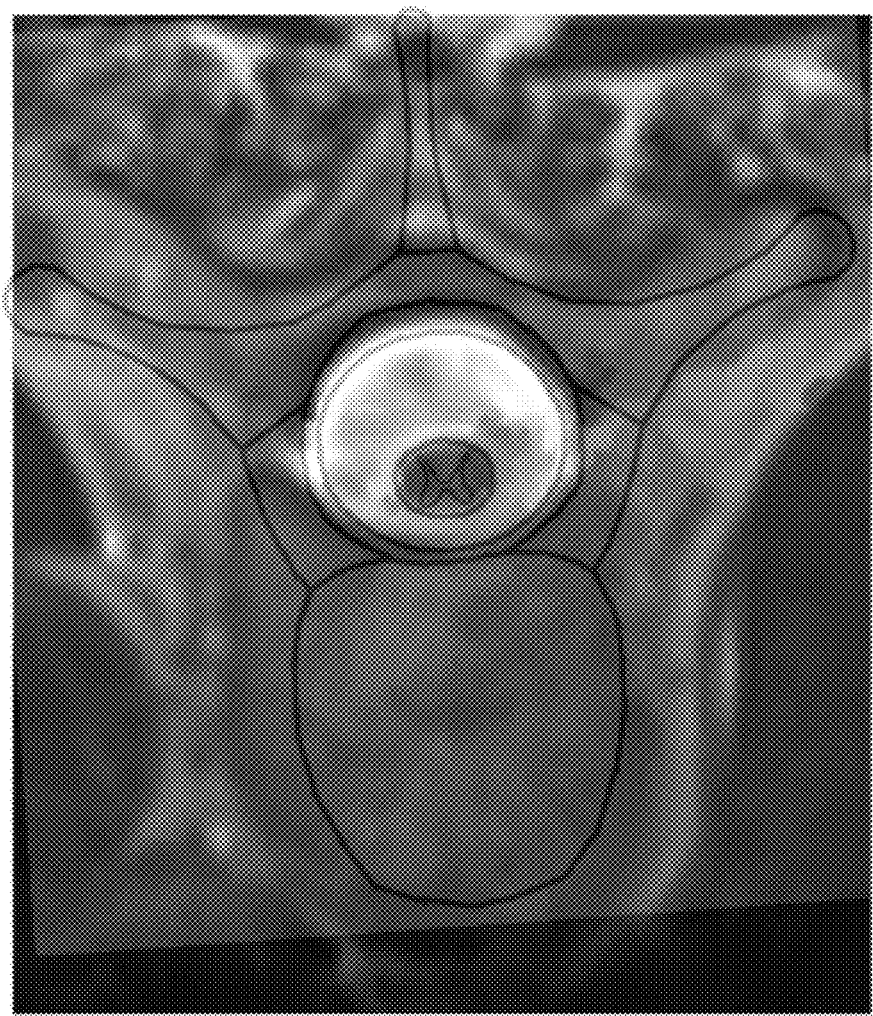
FIG. 2 is an image in which the transverse section of the modeled spine is overlaid with a transverse magnetic resonance image of the spine of a patient.
Figure 3:
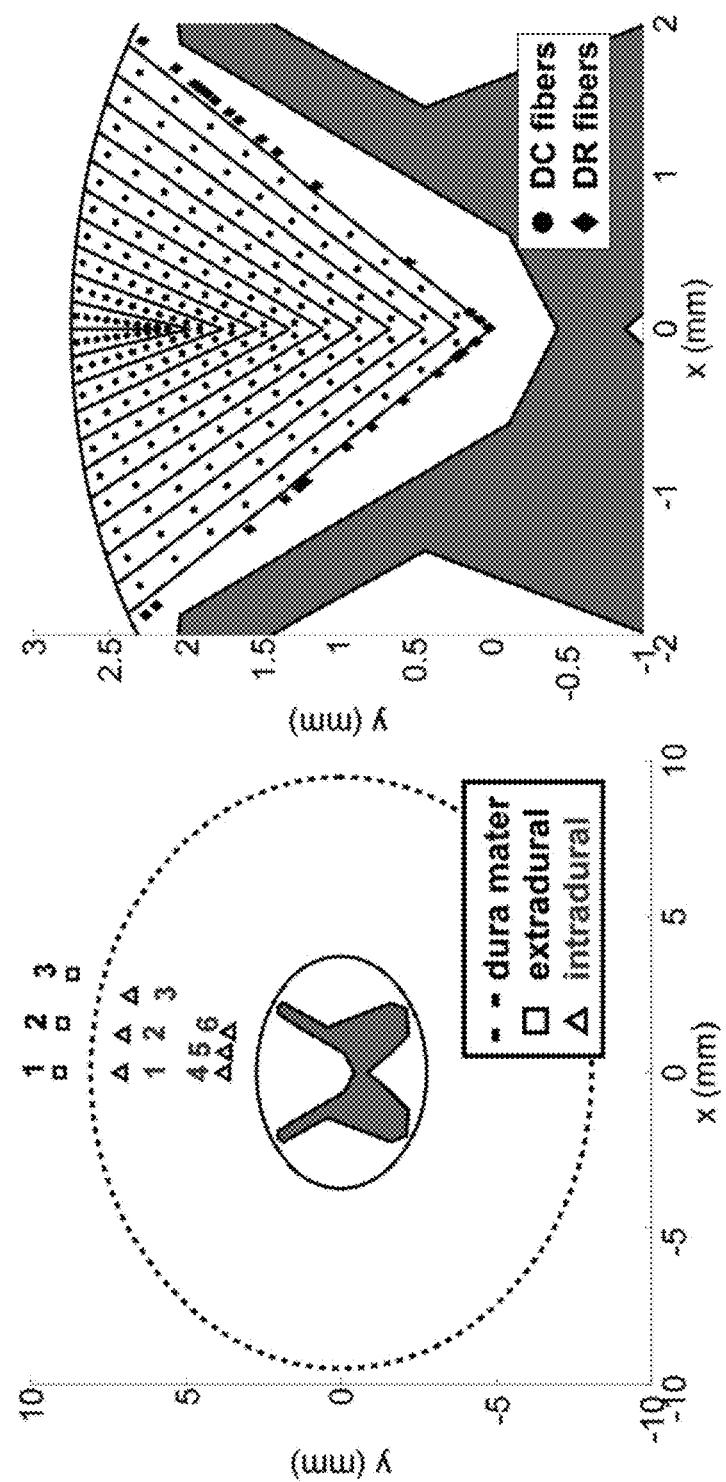
FIG. 3 is a diagram showing distribution of dorsal column (DC) fibers and dorsal root (DR) fibers within dorsomedial white matter of a spinal cord and stimulated with a percutaneous array in a bipolar configuration.

In accordance with embodiments of the present disclosure, an optimization method or process may begin by calculating the electric potentials generated during SCS. This may be accomplished by constructing a volume conductor model of a spine with an implanted electrode array. As an example, FIGS. 1A-1C illustrates different views of an example finite element model of a spine and spinal cord in accordance with embodiments of the present disclosure. More particularly, FIG. 1A illustrates a sagittal view of the modeled spine, FIG. 1B illustrates a transverse view of the modeled spine, and FIG. 1C illustrates a top perspective view of the modeled spine. The modeled spine, which may be made up of 12 vertebrae 100 spaced by disks 102, and a dural sac 104 and spinal cord 106 that traverse the spinal canal, may be placed inside of a rectangular prism (e.g., 100 mm×100 mm×300 mm) of homogeneous soft tissue, which is large enough to behave as an infinite conductive medium. Spinal dimensions are consistent with those of an adult human lower thoracic/upper lumber spine. Because neural tissue can be approximated as primarily resistive for typical SCS parameters, all tissues were modeled as purely conductive using electrical properties taken from published data. FIG. 2 illustrates an image in which the transverse section of the modeled spine is overlaid with a transverse magnetic resonance image of the spine of a patient. Modeled arrays were placed either within the epidural or intradural space of the spine as shown in FIG. 3, which illustrates a diagram showing distribution of DC fibers and DR fibers within dorsomedial white matter of a spinal cord (right) and stimulated with a percutaneous array in a bipolar configuration at 9 different locations: 3 epidural locations and 6 intradural locations (left). The potentials generated by the stimulating electrodes were calculated by using the finite element method (FEM) to numerically approximate the solution to Laplace's equation (Equation 1):

$$\nabla^2 \Phi = -\nabla \cdot (\rho \cdot \vec{J}) = 0 \quad (1)$$

A subsequent step in the optimization method includes simulating the response of cable models of DC and DR fibers to the electric potentials calculated with the volume conductor model. The dorsomedial white matter of the spinal cord (i.e., between the dorsal boundaries of the cord and grey matter) was split into 11 dermatomes based on the mediolateral segmental lamination of DC fibers. Twenty (20) DC fibers were bilaterally distributed (10 on either side of the transverse midline) within the 10 most medial dermatomes, for a total of 200 DC fibers—originating from distal, caudal DR fibers, which were not modeled. An additional 200 DC fibers were bilaterally distributed in the lateral-most dermatome, but these fibers were attached to the proximal end of 200 corresponding DR fibers. DR fibers descended about the dorsal aspect of the spinal cord in a ventrolateral direction (i.e., via the rootlets) and exited the spine through the intervertebral foramina. This is depicted in FIG. 3.

The diameters of myelinated fibers in the dorsomedial white matter range between 1-15 µm. Although the vast majority (greater than 60%) of the fibers have diameters between 1-6 µm, computational modeling studies have shown that the thresholds of the larger diameters fibers (about 12 µm) can better explain the threshold observed in SCS. Therefore, a suitable fiber diameter (e.g., 9 µm) may be used for both the DC fibers and DR fibers. The DC fibers and DR fibers may be stimulated with a 300 µs monophasic rectangular pulse, consistent with typical pulse widths (about 60-600 µs) used in SCS. Due to linearity of the conductive medium, the potentials at a given stimulus amplitude were calculated by multiplying the FEM solution by a scalar. The stimulation threshold voltage for each fiber was calculated using a bisection algorithm (relative error <1%), and input-output curves of the activated population as a function of the stimulation amplitude/power were constructed.

A subsequent step (and final step in some examples) in the optimization process includes using the results from the coupled FEM and cable models to evaluate and minimize a cost function via a numerical optimization algorithm. In an example, a genetic algorithm (GA) may be used. The GA may begin, for example, with a population of 20 randomly generated parameter sets defining the electrode configurations, and the performance of each configuration may be assessed. Stimulation selectivity may be quantified by constructing a curve, $p(x)$, of the proportion of a non-target population, the DR fibers, activated versus selected proportions of a target population, the DC fibers, and calculating the area (Equation 2) under the curve:

$$A = \int p(x)dx. \quad (2)$$

Stimulation efficiency may be quantified by calculating the electrical energy (Equation 3) consumed by the stimulation pulse in activating the target DC fibers.

$$E = \int I(t)V(t)dt, \quad (3)$$

where 1 and V are the applied stimulation voltage and current, respectively. The fitness (i.e., cost) of each electrode configuration can be a scaled linear or non-linear combination of Equations 2 and 3, where each term may be weighted equally or differently to optimize differentially electrode configurations for efficacy (selectivity) or efficiency.

After the initial fitness evaluation, each subsequent generation can include the two (2) fittest solutions from the previous generation and eighteen (18) new solutions created through genetic recombination of 18 different pairs of solutions from the previous generation, where more fit solutions have a higher probability of being represented in these crossings. The GA terminates when the average change in the cost function is <0.1% over 100 generations, or after 200 generations. Optimizations may be repeated 10 times, for example, to determine if the optimal solution is a local or global optimum.

Model-based optimization may be carried out offline, before the patient is implanted with the SCS device. Initially, pre-operative magnetic resonance (MR) or computer tomography (CT) images may be used to construct a patient-specific model of the spine—similar to what has been proposed for brain stimulation therapies. The geometry of the spinal structures are defined by mapping a three-dimensional atlas of the spine to the pre-operative images of the patient; and the electrical properties of the spinal regions, as well as the trajectories of the DC fibers and DR fibers, may be determined using diffusion-tensor MR imaging, from published literature, or from an anatomical atlas. Subsequently, the patient-specific model may be coupled with a numerical optimization algorithm (e.g., genetic algorithm) to determine the optimal intradural electrode position and electrode configuration (contact number, contact geometry, and contact polarity) for maximal activation of the targeted DC fibers (maximal pain coverage of the target dermatome). Optimal solutions are those that use as little energy (e.g., Equation 3) as possible to activate the target DC fibers with minimal co-activation of DR fibers and/or non-target DC fibers (e.g., Equation 2).

Figure 4:
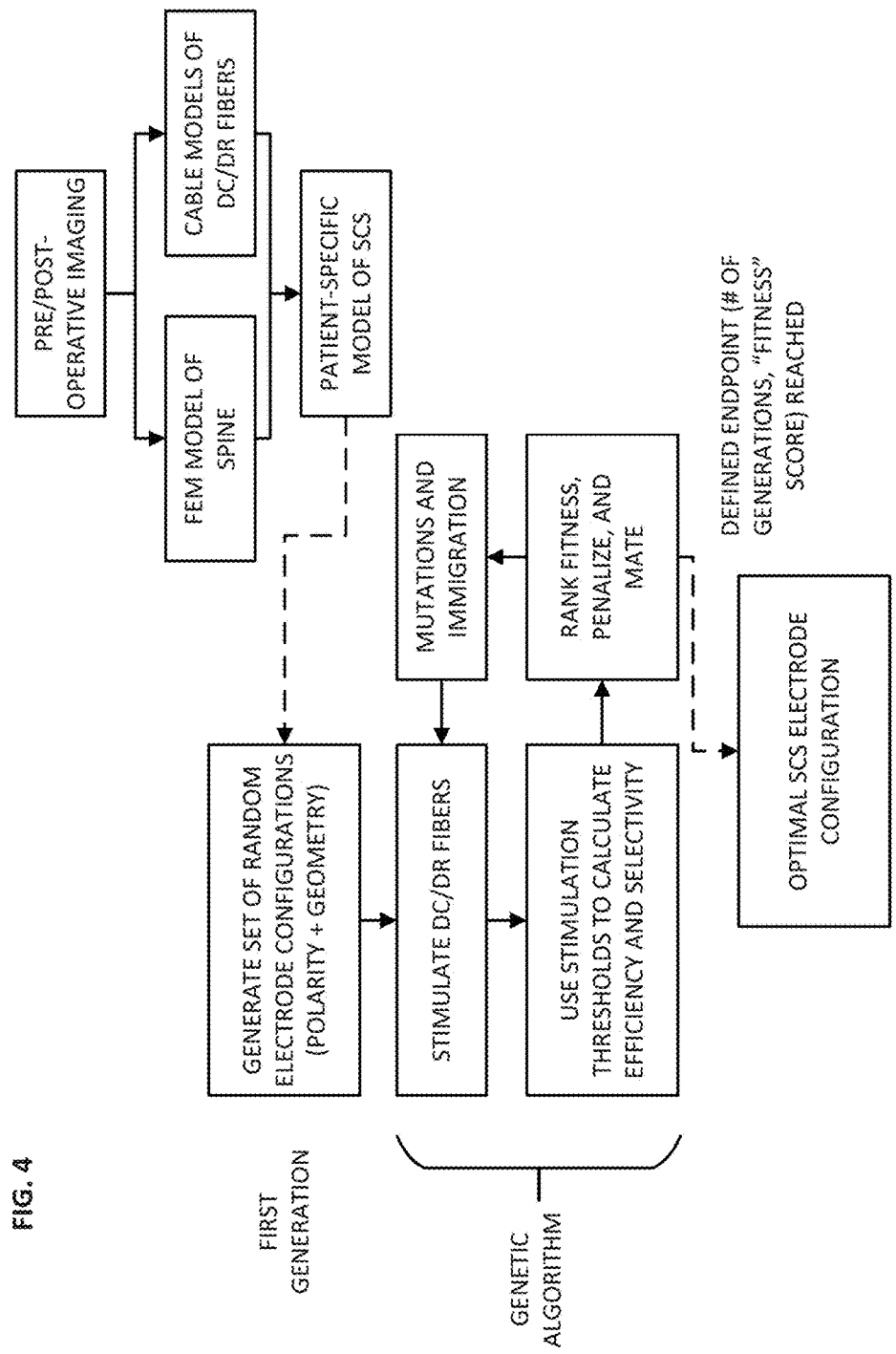
FIG. 4 is a flow chart depicting this example method of model-based optimization of SCS electrode designs in accordance with embodiments of the present disclosure.

Offline model-based optimization of the electrode configuration can also be carried out post-operatively throughout the course of the therapy. This can be advantageous because the tissue response to the electrode (e.g., scarring and edema) and its movement in the cerebral spinal fluid (CSF) can have an effect on the optimal electrode configuration. First, post-operative imaging is used to assess the tissue response, its effect on the position of the spinal cord and electrode, and the extent to which the implanted array has migrated. Subsequently, the post-operative imaging data is used to update the patient-specific model and the numerical optimization algorithm is used to ascertain if a more optimal solution exists. If a more optimal electrode configuration does not exist, the optimization algorithm can be run again to assess the prospective benefits of a revision surgery to reposition or replace the lead. FIG. 4 illustrates a flow chart depicting this example method of model-based optimization of SCS electrode designs in accordance with embodiments of the present disclosure.

In experiments, five (5) SCS models of patients that had undergone acute intraoperative evaluation of epidural and intradural SCS. The geometries of the spinal cord and dural sac, as well as the position of the cord within the sac, were matched to the pre-operative MR images of the corresponding patients. The geometry of the spinal column did not vary across patients and reflected the geometry of an average adult human lower thoracic/upper lumbar spine. Similar to what was clinically, SCS was administered by delivering 300 µs current pulses with a percutaneous array in a bipolar electrode configuration, where the cathode was proximal to T8 and the anode was rostral to the cathode. Clinical sensory thresholds (i.e., when the patient first reported a paresthesia) were compared against theoretical sensory thresholds (i.e., the lowest threshold amongst DC fibers and DR fibers) to assess the predictive capabilities of the SCS model. The computational model predicted (1) the relative order of the stimulation thresholds, (2) the greater than about 5-fold difference between the epidural and intradural stimulation thresholds, and (3) the effect of the cord position on the stimulation thresholds.

Figure 5:
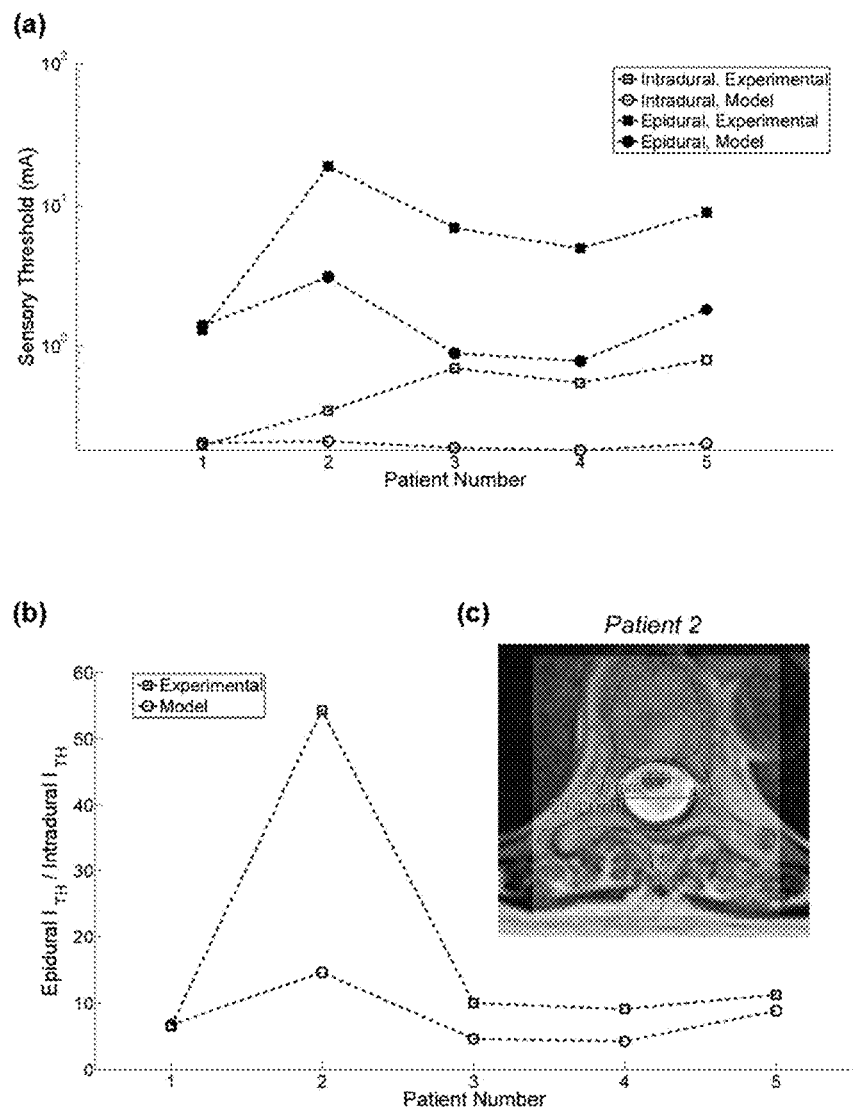
FIG. 5 are graphs and an image depicting a comparison of model predictions to experimental results.

FIG. 5 illustrates graphs and an image depicting a comparison of model predictions to experimental results. (a) of FIG. 5 shows a plot of sensory thresholds measured clinically (i.e., when the patient first reported a paresthesia) and calculated theoretically (i.e., the lowest threshold amongst DC fibers and DR fibers) during epidural and intradural SCS. (b) of FIG. 5 shows the ratio of epidural sensory thresholds ($I_{TH}$) to the intradural $I_{TH}$. (c) of FIG. 5 shows the transverse cross-section of the modeled spine of a patient overlaid on its corresponding pre-operative MR image.

Further computational simulations were conducted to assess the theoretical performance (efficiency and selectivity) of intradural SCS versus epidural SCS and how sensitive the performance of SCS was to variability in the electrode position and patient geometry. This was accomplished by analyzing the results of each patient-specific model at 9 different electrode locations: 3 epidural locations 1 mm above the dura, 3 intradural locations 1 mm below the dura, and 3 intradural locations 1 mm above the cord, with the 3 points in each of the above sets having lateral (clockwise) offsets of 0°, 10°, and 20° from the transverse midline, respectively (see FIG. 3).

Figure 6:
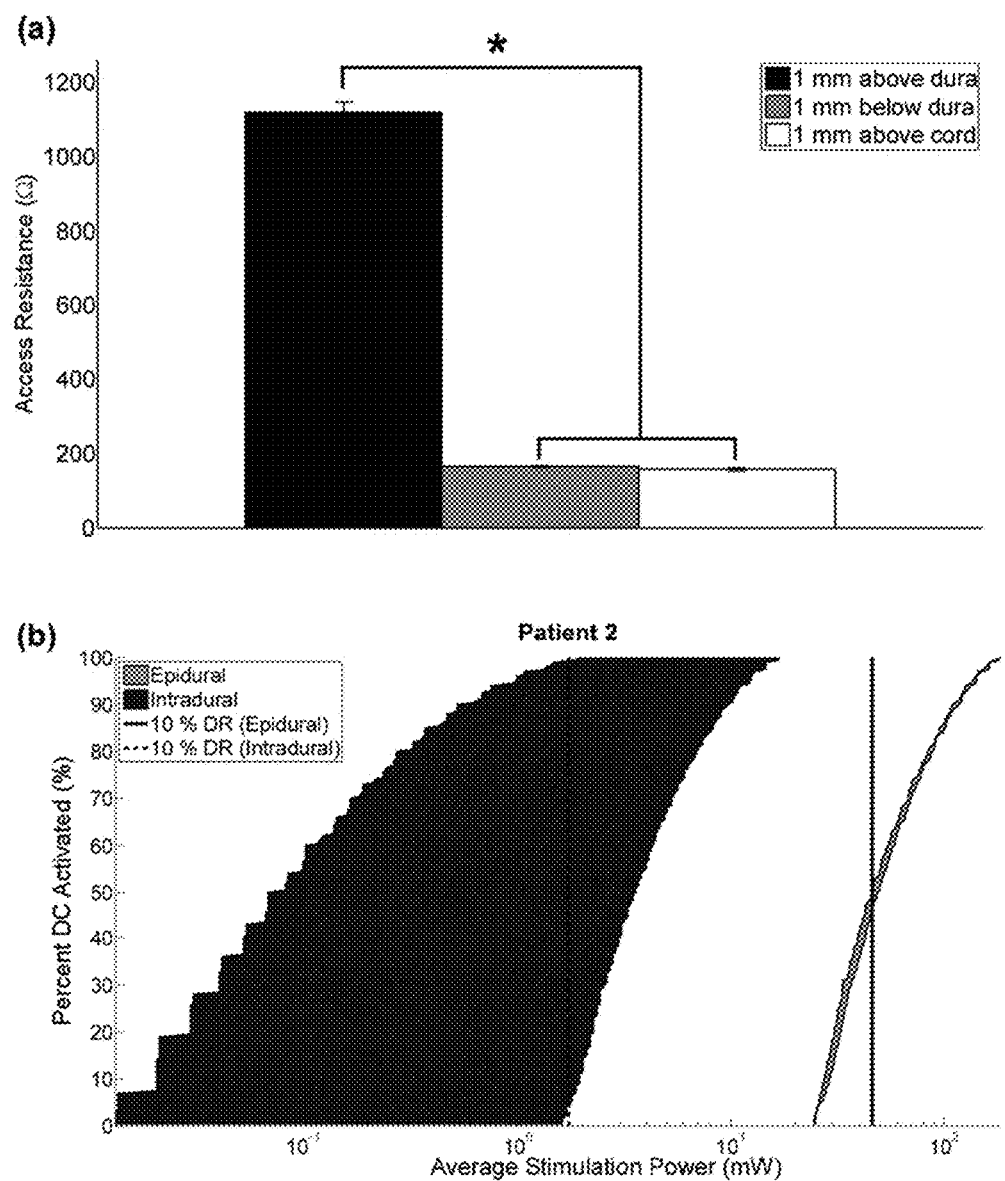
FIG. 6 are graphs showing the efficiency of epidural SCS versus intradural SCS.

The results show that efficiency of SCS was insensitive to variations in the spinal geometry of the patient but sensitive to the location of the electrode. The access resistance of the electrode ($R_a$) was insensitive to electrode movements within the epidural and intradural space, as its coefficient of variation (standard deviation/mean) was <0.06 across the 5 patients; however, $R_a$ decreased by about 85% when the electrode moved from the epidural space to the intradural space. FIG. 6 illustrates graphs showing the efficiency of epidural SCS versus intradural SCS. Particularly (a) of FIG. 6 shows the average access resistance ($R_a$)±1 standard error of the mean of the model percutaneous array in a bipolar configuration across 5 patients. $R_a$ in the epidural space is significantly greater ($\alpha$=0.05) than $R_a$ in the intradural space. Such a drastic reduction in $R_a$, along with increasing proximity of the electrode to the cord, reduced the average power consumption of intradural SCS>90%, compared with epidural SCS. (b) of FIG. 5 shows the average power required to stimulate the DC fibers. For reference, the average power required to activate 10% of the DR fibers is included. Therefore, intradural SCS can impact the efficacy of SCS by substantially increasing the battery lives of IPGs—and the recharge intervals of rechargeable IPGs.

Figure 7:
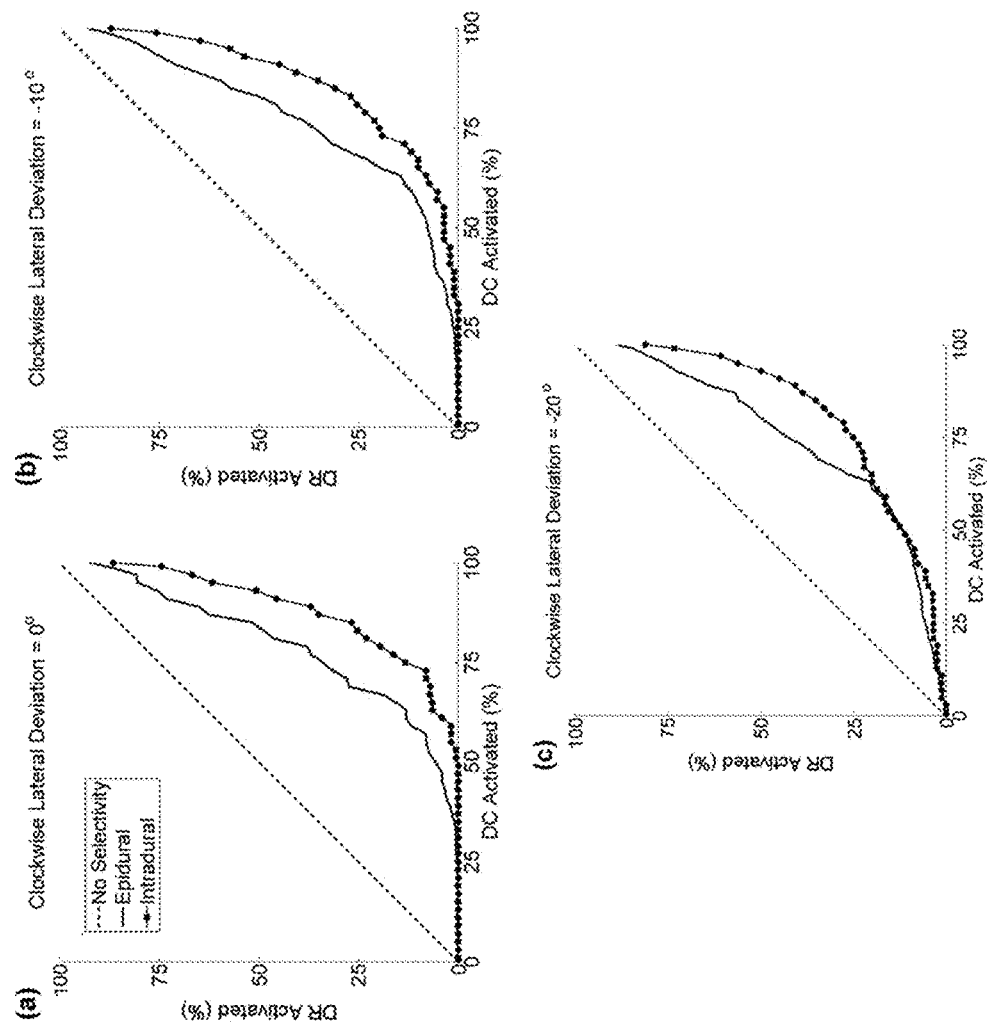
FIG. 7 are graphs showing selectivity of epidural SCS versus intradural SCS.

Selectivity, unlike efficiency, was sensitive to the position of the electrode. For both epidural and intradural SCS, better selectivity (i.e., activation of DC fibers without co-activation of DR fibers) was achieved when the lead was positioned medially along the transverse midline of the cord; however, between the two, the best selectivity was achieved with intradural SCS, as shown in (a) of FIG. 7. FIG. 7 illustrates graphs showing selectivity of epidural SCS versus intradural SCS. Particularly, the figure shows curves of the proportion of DR fibers activated versus proportions of the DC fibers when the modeled percutaneous array was laterally deviated (a) 0°, (b) −10°, and (c) −20° from the transverse midline. It is noted that negative angles denote clockwise rotations. For example, with epidural SCS and intradural SCS, 25% and 50% of the DC fibers may be activated before the first DR fiber was activated, respectively. However, as the lead was laterally displaced from the midline, the advantage gained in selectivity with intradural SCS declined (see (b) and (c) of FIG. 7). Therefore, in general, there is a tradeoff between selective activation of more lateral dermatomes and selectivity—or broad pain coverage.

Figure 8:
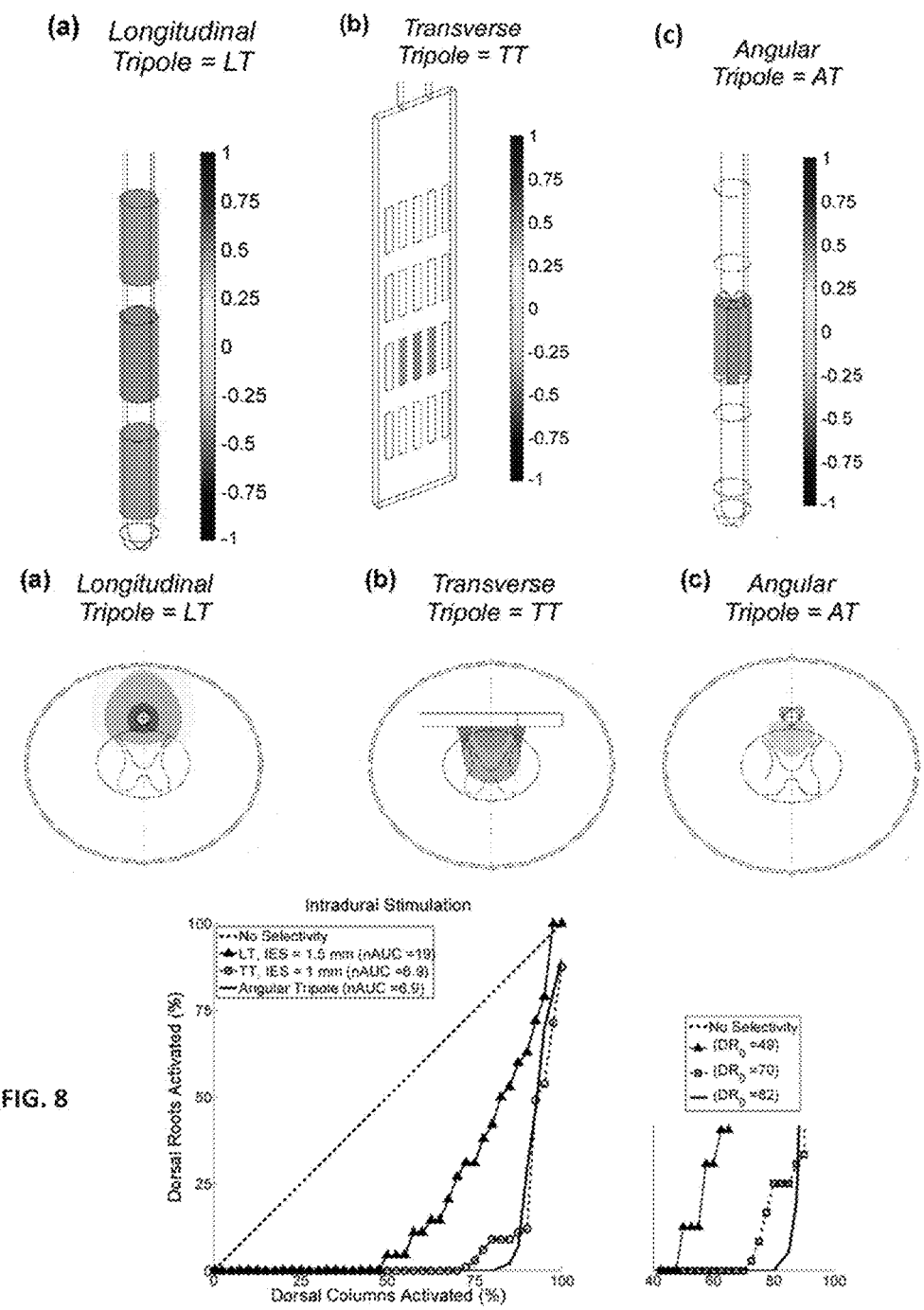
FIG. 8 are diagrams and graphs showing selectivity of intradural SCS electrode designs.

In another analysis, computational simulations were conducted to determine if novel electrode designs may be used to increase the performance of SCS. In this analysis, five (5) different electrode configures were tested: 2 Medtronic percutaneous leads, Models 3776/3876 and 3778/3878 (available from Medtronic Inc., of Minneapolis, Minn.), in longitudinal tripolar (LT) configurations; the Saint Jude MEDICAL PENTA™ (available from St. Jude Medical, Saint Paul, Minn.) in 2 different transverse tripolar (TT) configurations; and a system in accordance with the present disclosure, a cylindrical azimuthal array in an angular tripolar (AT) configuration as shown in FIG. 8, which illustrates diagrams and graphs showing selectivity of intradural SCS electrode designs. Particularly, (a) of FIG. 8 depicts an example percutaneous lead with an inter-electrode spacing of 1.5 mm, in a longitudinal tripolar (+, −, +) configuration (top) and filled isovalues contours of the potential distribution generated by this design in the intradural space (bottom). (b) of FIG. 8 depicts a PENTA™ and example percutaneous lead with an azimuthal array of electrodes in a tripolar configuration in the same format as shown in (a). (d) of FIG. 8 shows curves of the proportion of DR fibers activated versus selected proportions of the DC fibers for the designs shown in (a), (b), and (c). The normalized area under the curve (nAUC) and the percent of DC fibers activated with co-activation of DR fibers ($DR_0$) are used to quantify selectivity. All tested configurations had better selectivity when placed within the intradural space. The TT had better performance than the LT in selectively activating DC fibers over DR fibers, and the AT had better performance than the TT (FIG. 7d)—although at the expense of higher energy consumption. These results suggest that more optimal electrode designs exist for increasing the performance of SCS.

A subsequent step may be to couple the computational model of SCS with a GA to provide a cylindrical lead design which may be placed percutaneously that not only has better selectivity than the paddle lead in a TT configuration, but also consumes less energy. Initial modeling work has shown that this may be possible using a cylindrival lead with an azimuthal array of electrodes in a multipolar configuration. There are several reasons why using a cylindrical design which may be placed percutaneously (PERC) is advantageous. First, implantation of PERC leads is less invasive compared to paddle leads, so there is less risk associated with implantation surgeries, such as infection. Second, PERC leads, although more likely to migrate over time, are less prone to breaking. And third, there may be potentially less scarring of the PERC lead, because PERC leads are smaller than paddle leads and the tissue response to the electrode depends on its size.

In accordance with embodiments, the FEM was used to construct a volume conductor model of the spinal cord and an implanted three-contact percutaneous electrode array in COMSOL Multiphysics v3.4 (COMSOL Inc., Burlington, Mass.) as shown in the example of FIGS. 1A-1C. Three electrodes were chosen to enable monopolar (−), bipolar (+ −), and tripolar (+ − +) configurations. The model spine consisted of 12 vertebrae, thoracic level 3 (T3) to lumbar level 2 (L2), spaced by disks, and a dural sac and spinal cord that traversed the spinal canal. The model spine was placed within a rectangular prism of homogeneous soft tissue that was large enough (100 mm×100 mm×300 mm) to behave as an infinite conducting medium. Spinal dimensions were consistent with those of an adult human lower thoracic/upper lumbar spine. All tissues were modeled as purely resistive, with electrical conductivities from published data (Table 1).

A Delaunay triangulation algorithm was used to discretize the FEM model into a graded mesh of Lagrange tetrahedral cubic elements, where the mesh density was greatest near the electrode surfaces, spinal cord, and dura mater. The shaft of the array was assumed to be perfectly insulating and was modeled as a boundary layer with zero normal current density (i.e., Neumann boundary condition). Monopolar stimulation was modeled by applying potentials of 1 V and 0 V (i.e., Dirichlet boundary conditions) on the surface of the stimulation electrode and outer surface of the tissue volume, respectively. Bipolar and tripolar configurations were modeled by applying potentials of +1 V and −1 V and +1 V, −1 V, and +1 V to either 2 or 3 consecutive contacts, respectively. In the bipolar and tripolar cases, the cathode served as the return, and the outer tissue boundary was assumed to be perfectly insulating. The electric potentials (Φ) generated in the tissue by the electrode array were calculated by solving Laplace's equation (Equation 4):

$$\nabla \cdot (\sigma \cdot \nabla \Phi) = -\nabla \cdot \vec{J} = 0 \quad (4)$$

where $\nabla$ is the divergence operator, $\sigma$ is the conductivity tensor, and $\vec{J}$ is the current density. The applied current was calculated by integrating the current density (Equation 5) on the surface of electrodes with positive applied potentials (i.e., anodes):

$$\vec{J} = \sigma \cdot \vec{E} \quad (5)$$

where, $\vec{E}$ is the electric field. The lumped resistance of the tissue, also known as the series or access resistance ($R_a$), was calculated by dividing the voltage between the anode and cathode by the applied current.

TABLE 1

Electrical conductivity of tissues represented in volume conductor model of spinal cord stimulation

| Tissue | Conductivity (S/m) |
| --- | --- |
| White matter, longitudinal | 0.60 |
| White matter, transverse | 0.083 |
| Grey matter | 0.23 |
| Cerebrospinal fluid | 1.8 |
| Dura mater | 0.030 |
| Extradural space[a] | 0.20 |
| Vertebral bone | 0.02 |
| Intervertebral disc | 0.65 |
| Muscle[b] | 0.20 |

[a]The lumped conductivity of the extradural space was assumed to be similar to that of muscle.
[b]tissue surrounding spine.

A NEURON (v7.1) simulation environment was used to implement cable models of DC and DR fibers, and to calculate their response to modeled SCS. Two different non-linear cable models of axons with Hodgkin-Huxley-type ion channels were used: a mammalian axon model with perfectly insulating myelin, the Sweeney (SW) model, which was used in previous computational models of SCS; and a more detailed model of a myelinated mammalian axon, the McIntyre, Richardson and Grill (MRG) model, which takes into account the structure and electrical properties of the myelin.

Because the myelin in the SW model is assumed to be perfectly insulating, only the nodes of Ranvier (NoR) and internodal resistance were modeled. The membrane at each NoR contained a parallel combination of a nonlinear sodium conductance, a linear leakage conductance, and a membrane capacitance. In the MRG model, each NoR contained fast and persistent sodium conductances, a slow potassium conductance, a linear leakage conductance, and a membrane capacitance; and the membrane underneath the myelin contained a linear leakage conductance and a membrane capacitance.

Figure 9A:
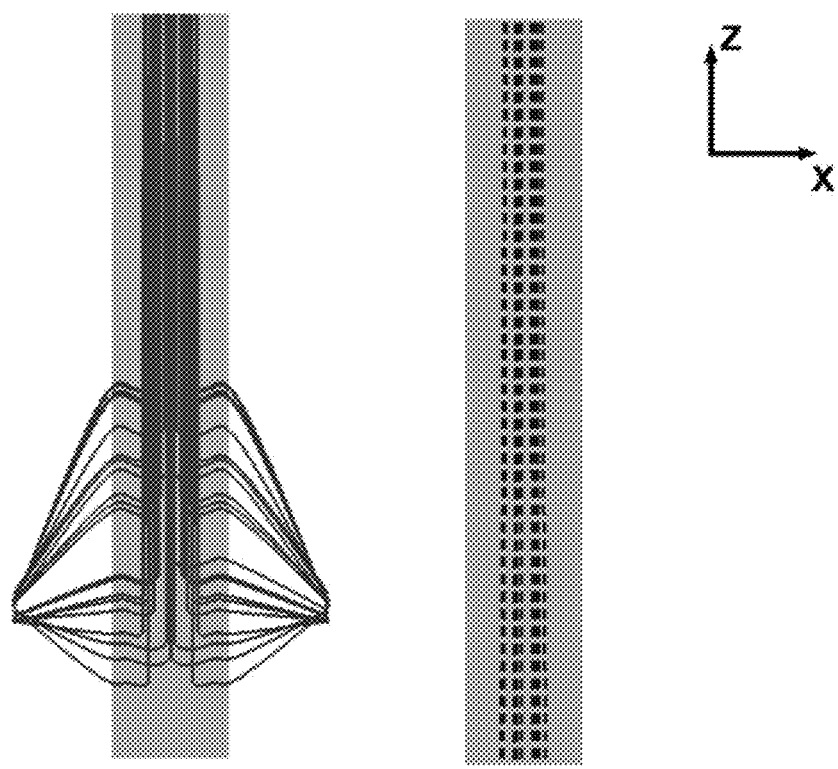
FIGS. 9A and 9B illustrate planar dorsal and lateral views and a three-dimensional (3D) view, respectively, of example modeled DC fibers and DR fibers.
Figure 9B:
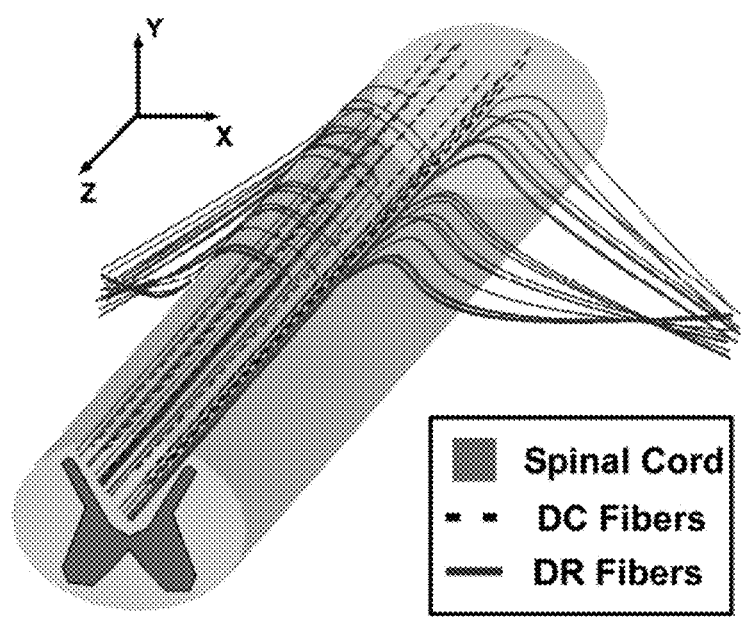

The dorsomedial white matter of the spinal cord (i.e., between the dorsal boundary of the spinal cord and the grey matter) was split into 11 dermatomes based on the mediolateral segmental lamination of DC fibers. A total of 200 DC fibers were bilaterally distributed—10 fibers within each of the 10 most medial dermatomes on either side of the transverse midline (see right side of FIG. 3)—representing collaterals that originated from distal, caudal DR fibers, which were not modeled. An additional 200 DC fibers were bilaterally distributed in the lateral-most dermatome, and these fibers were attached to the proximal end of 200 corresponding DR fibers. DR fibers descended from the dorsal aspect of the spinal cord in a ventrolateral direction (i.e., via the rootlets) and exited the spine through the intervertebral foramina (see FIGS. 9A and 9B). FIGS. 9A and 9B illustrate planar dorsal and lateral views and a 3D view, respectively, of example modeled DC fibers and DR fibers.

The diameters of myelinated fibers in the dorsomedial white matter range between 1-15 μm. Although the vast majority (>60%) of the fibers have diameters between 1-7 μm, prior computational modeling studies have shown that fibers as large as 12 μm are activated within the therapeutic range of in SCS. Nine separate populations of 200 DC fibers with diameters of 3, 6, 9, 12 and 15 μm, and nine separate populations of 200 DR fibers with the same diameters have been considered.

Figure 10:
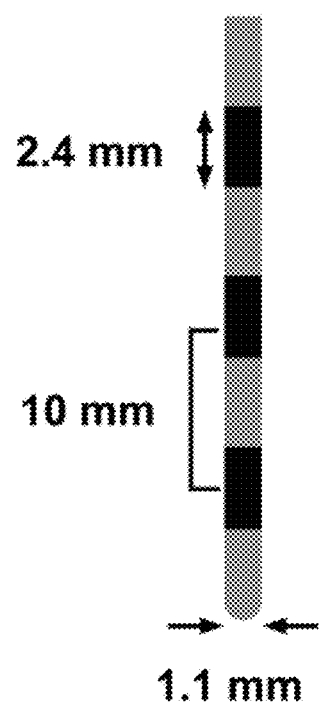
FIG. 10 is a diagram of an example modeled percutaneous array that was placed in the nine different locations shown in the left side of FIG. 3.

Potentials were calculated using the maximum possible number of cubic elements (~1.34 million) with 8 GB of memory. Refinement of the FEM mesh (i.e., splitting elements into smaller elements) from ~635,000 to 1.34 million cubic elements resulted in errors of <1% in the potentials and corresponding stimulation thresholds of the modeled fibers, where error was defined as the mean absolute relative difference between the refined solution and the solution prior to refinement. Similarly, doubling the tissue volume yielded errors of <2% and <1% in the potentials and stimulation thresholds of the modeled fibers, respectively. FIG. 10 illustrates a diagram of an example modeled percutaneous array that was placed in the nine different locations shown in the left side of FIG. 3.

Five subjects were enrolled in a controlled exploratory study of acute SCS trial system implantation (NCT02020460 on clinicaltrials.gov). Subjects were injected with a local anesthetic in the lower back, and a sedative was administered intravenously. Fluoroscopy was used to guide placement of an eight-contact extradural trial lead, the Spencer Probe Depth Electrode (AD-TECH Inc., Racine, Wis.) (see FIG. 10), in the extradural space and pick five consecutive contacts that spanned the vertebral levels of interest, T8-T10. The extradural array was connected to an external stimulator (MTS, St. Jude Medical, Saint Paul, Minn.), and stimulation was delivered in a bipolar configuration between the two contacts closest to T8, where the rostral cathode and caudal anode were proximal and distal to T8, respectively. Stimulation waveforms were current-regulated, asymmetric pulses with a short 300 μs positive phase followed by a long 700 μs negative phase delivered at 60 Hz.

A staircase paradigm was used to determine sensory and discomfort thresholds. First, a reference for paresthesia was established: the stimulation amplitude ($I_A$) was increased in 1 mA increments from 0 mA until the subject reported a sensation (i.e., S), and $I_A$ was decreased in decrements of 1 mA until S was no longer perceived. The subject was asked to describe orally the location of S. Second, $I_A$ was increased in 0.1 mA increments until S was reported, defined as $I_{S1}$. Third, $I_A$ was decreased in 0.1 decrements until S went away, defined as $I_{S2}$. Fourth, $I_A$ was increased in 0.1 mA increments until S was reported, defined as $I_{S3}$. The sensory threshold was defined as the average of $I_{S1}$, $I_{S2}$, and $I_{S3}$. Finally, $I_A$ was increased in increments of 0.1 mA until the subject reported discomfort and/or pain, which was defined as the discomfort threshold. As $I_A$ was increased, the subject was asked to describe orally any additional locations of S.

After sensory and discomfort thresholds were measured in the extradural case, fluoroscopy was used to place the AD-TECH array within the dura in a fashion similar to insertion of a standard lumber drain catheter, and the array was connected to the external stimulator. As in the extradural case, current-regulation stimulation was delivered at 60 Hz between the two contacts most proximal to T8, and the staircase paradigm was used to determine sensory and discomfort thresholds.

Five models of SCS were constructed based on the individual spinal cord dimensions of patients that had undergone acute intraoperative evaluation of extradural and intradural SCS. Preoperative magnetic resonance imaging (MRI) scans of the corresponding patients were used to measure the geometries of the spinal cord and dural sac, and the position of the cord within the sac (Table 2). The geometry of the modeled spinal column did not vary across patients and reflected the geometry of an average adult human lower thoracic/upper lumbar spine (see FIG. 1).

Patient-specific models were evaluated at nine different electrode locations (see FIG. 3): three extradural locations 1 mm above the dura, three intradural locations 1 mm below the dura, and three intradural locations 1 mm above the spinal cord, where points one, two, and three in each set had lateral (clockwise) offsets of 0°, −10°, and −20° from the transverse midline, respectively.

Clinical conditions were emulated by stimulating the model DC and DR fibers with a 300 μs monophasic rectangular pulse, consistent with typical pulse widths (175-600 μs) used in SCS. The cathode was proximal to T8, and the distal anode was rostral to the cathode. Due to linearity of the solution, the potentials at a given stimulus amplitude were calculated by multiplying the base (monopolar, bipolar, or tripolar) solution by a scalar. The stimulation threshold voltage for each fiber was calculated using a bisection algorithm (relative error <1%). The stimulation threshold current was calculated by dividing the threshold voltage by $R_a$, and input-output curves of the number of activated model nerve fibers as a function of the stimulation amplitude and stimulation power were constructed.

The stimulation thresholds of the MRG and SW model fibers were compared to the clinically measured sensory thresholds, when the patient first reported a paresthesia, and the discomfort threshold, when the patient first reported pain or discomfort. The following procedure was used to determine the percentage and diameter of DC fibers that most closely matched the clinical findings. First, for each diameter, we calculated the percentage of DC fibers activated at the sensory and discomfort thresholds. Next, because two hundred model DC fibers were evenly split across 20 laminae (see FIG. 3), the clinical findings were translated into an expected percent activation by assuming that paresthesia in one dermatome on one side of the body corresponded to activation of 5% of the modeled DC fibers. The DC fiber population (of a given diameter) that best matched clinical findings was defined as the one whose percent activation at the clinical thresholds most closely matched the expected percent activation based on the number of dermatomes reported at the clinical thresholds.

TABLE 2

Spinal Cord Geometry from Individual Patients[a]

| Patient | Spinal Cord Dimensions (mm) | | CSF Space Dimensions (mm) | | Spinal Cord Placement[b] |
|---|---|---|---|---|---|
| | Medio-lateral | Ventro-dorsal | Medio-lateral | Ventro-dorsal | |
| 1 | 7 | 6 | 19 | 16 | center[c] |
| 2 | 8 | 7 | 21 | 18 | ventral[d] |
| 3 | 8 | 6 | 20 | 14 | center |
| 4 | 9 | 6 | 18 | 13 | center |
| 5 | 8 | 6 | 18 | 15 | ventral |

[a]Geometries were measured from MRI images (at 1.5 Tesla) with a resolution of 1 mm.
[b]Placement with respect to midline
[c]Spinal cord center placed at the center of the elliptical shell defining the dura mater
[d]The spinal cord center was twice as far from the dorsal interior surface of the dura mater as it was from the ventral interior surface of the dura mater The model of SCS was used to quantify the efficiency and selectivity of stimulation. Stimulation efficiency was quantified by calculating the average electrical power (Equation 3) consumed during the stimulation pulse to activate the target DC fibers:

$$\overline{P} = PW^{-1} \int_0^{PW} \frac{V^2(t)}{R_a} dt, \qquad (6)$$

where V(t) is the applied voltage, and PW is the duration of the rectangular pulse.

Selectivity was quantified using two different metrics: neural-element selectivity was analyzed by calculating the percent of DC fibers activated with no activation of DR fibers ($DC_0$) or with activation of a certain percentage (X) of DR fibers ($DC_X$), and dermatome selectivity was analyzed by determining if DC fibers in target dermatomes could be activated without activation of DC fibers in non-target dermatomes. Since the computational models were based on data from patients receiving SCS for the treatment of chronic low back pain, the low back dermatomes, L2-L5, were chosen to assess dermatome selectivity.

In addition to analysis with the lead (AD-TECH Spencer Probe Depth Electrode) used in the clinical experiments, simulations were conducted to test the extradural and intradural performance of five different electrode designs (FIG. 11): LT-1.5 and LT-6, which are two percutaneous leads, Medtronic Models 3776/3876 and 3777/3877 (Medtronic Inc., Minneapolis, Minn.), in longitudinal tripolar configurations with an inter-electrode spacing (IES) of 1.5 mm and 6 mm, respectively; TT-1 and TT-3, which are the St. Jude Medical PENTA™ (St. Jude Medical, Saint Paul, Minn.) in two transverse tripolar configurations with an IES of 1 mm and 3 mm, respectively; and a design in accordance with the present disclosure.

Figure 11:
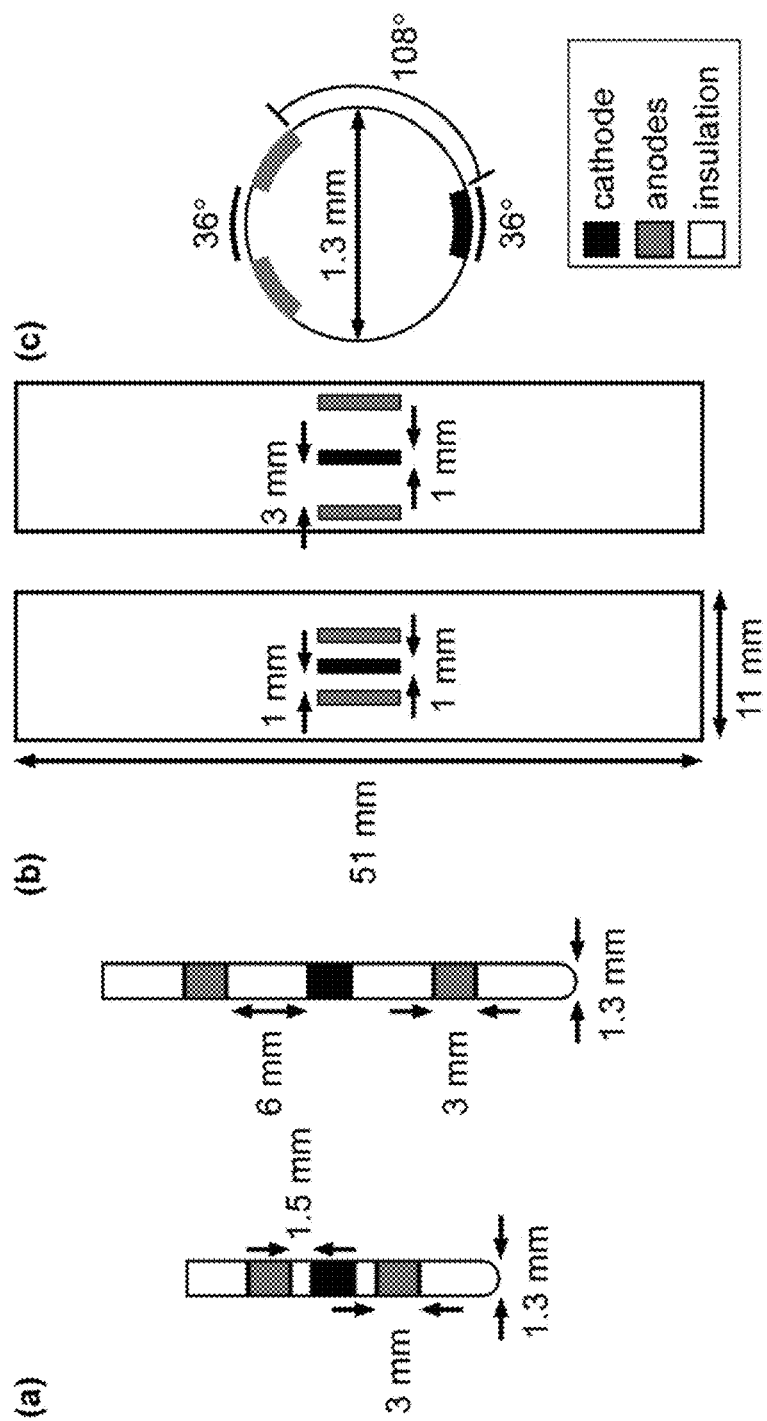
FIG. 11 are diagrams of five example SCS electrode designs evaluated with the computational model.

FIG. 11 illustrates diagrams of five example SCS electrode designs evaluated with the computational model. Particularly, (a) of FIG. 11 shows Medtronic Models 3776/3876 (left) and 3777/3877 (right) in longitudinal tripolar configurations. (b) of FIG. 11 shows a St. Jude Medical PENTA™ in two transverse tripolar configurations. (c) of FIG. 11 shows a transverse view of an example percutaneous lead with an azimuthal array of electrodes in a tripolar configuration. Inactive contacts were not represented.

TTs are believed to have greater selectivity than LTs because their distal anodes hyperpolarize the DR fibers, termed anodal shielding. However, it is believed that the superior selectivity of TTs over LTs arose from their ability to steer current away from DR fibers so that the potentials decayed more rapidly with increasing distance from the cathode. To test this, a fifth tripolar design, a percutaneous azimuthal array in an angular tripolar (AT) configuration was modeled, which had a cathode adjacent to the dorso-medial aspect of the spinal cord and anodes that directed current away from the cord, toward the dorsal aspect of the dura (see FIG. 11). The performance of all five designs was assessed with the each electrode array placed along the transverse midline, extradurally 1 mm above the dura mater and intradurally 1 mm above spinal cord (see FIG. 3).

The computational models of Patients 1-5 account for the effects of anatomical variability in the spinal geometry across patients. Yet, five sets of spinal geometries were not sufficient to determine if the geometrical parameters and subsequent output metrics (e.g., $R_a$ and $DC_O$) varied normally across patients, so we used a Kolmogorov-Smirnov (K-S) test to determine differences in the distributions of the output metrics across Patients 1-5. The K-S test assumes nothing about how the output metrics are distributed, and all K-S tests were run at a significance level of 5% ($\alpha$=0.05).

Linear regression and subsequent calculation of coefficients of determination ($r^2$) were used to determine whether the variability in the sensory and discomfort thresholds could be explained by differences in anatomical measurements across patients.

Five patient-specific models of SCS, compared the model stimulation thresholds to clinical stimulation thresholds, and used the models used to quantify the efficiency and selectivity of both intradural and extradural SCS.

Figure 12:
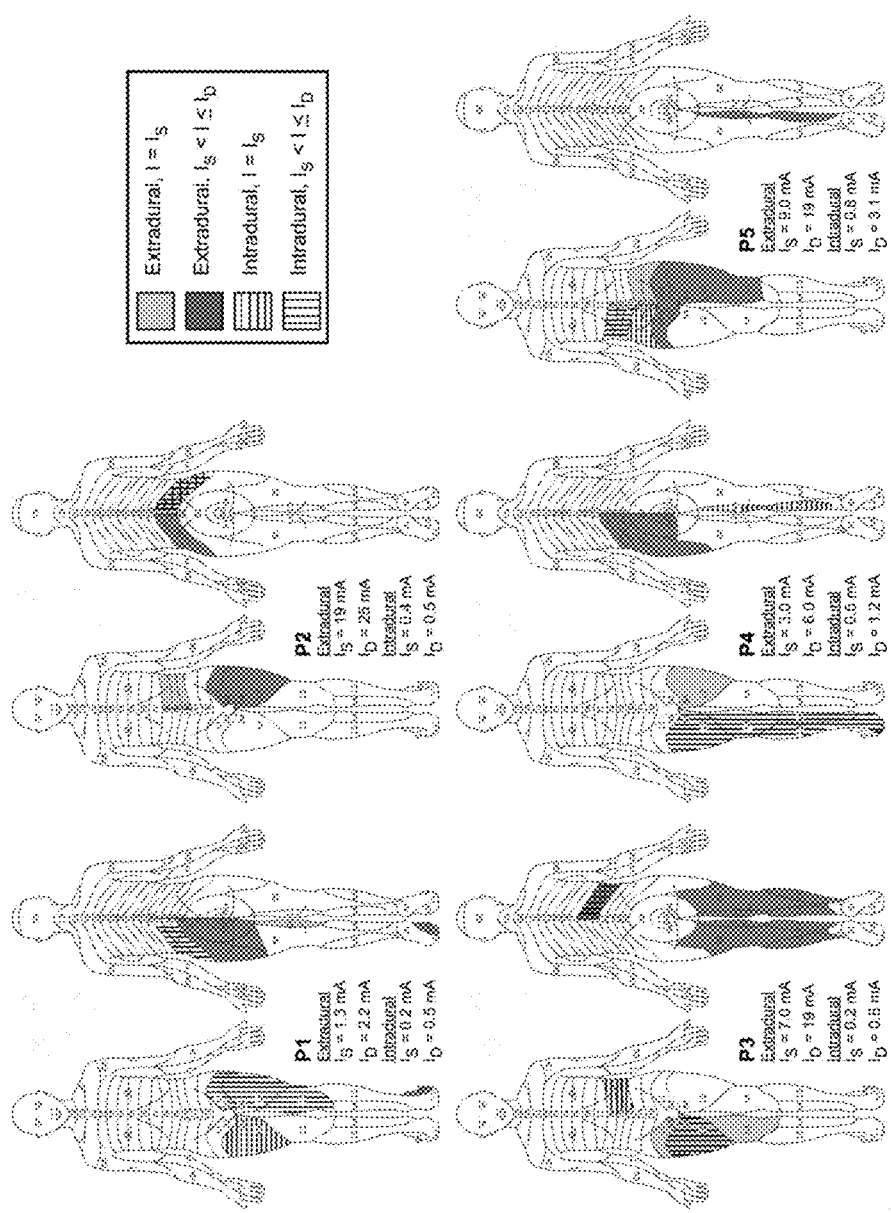
FIG. 12 shows diagrams of reported locations of paresthesias in Patient 1-5.

Paresthesias at the sensory thresholds of Patients 1-5 were reported in the legs, middle and lower back, buttocks, belly, and waistline region (FIG. 12). FIG. 12 shows diagrams of reported locations of paresthesias in Patient 1-5. Paresthesias in each patient (P) were charted based on their oral descriptions at the sensory thresholds (Is) and increasing amplitudes until the discomfort threshold ($I_D$) was reached. In Patients 1, 4, and 5, the location of paresthesia differed between the intradural and extradural cases; whereas in Patients 2 and 3, the locations of the paresthesia in the two cases overlapped. In all patients, as the stimulation amplitude increased, paresthesias were reported in additional locations. The quality of the paresthesias and the location of discomfort were not determined.

The sensory thresholds across all patients ranged from 0.2-0.8 mA and 1.3-19 mA in the intradural and extradural cases, respectively, whereas the discomfort thresholds ranged from 0.5-3.1 mA and 2.2-25 mA (see FIG. 12). Distributions of the sensory and discomfort thresholds across patients were not significantly different within the intradural and extradural cases. However, between the intradural and extradural cases, the distributions of sensory (p<0.01) and discomfort (p<0.05) thresholds across patients were significantly different.

The extradural sensory thresholds showed a strong linear correlation ($r^2$>0.80, p<0.07) with the ventrodorsal width of the CSF space and the ventral displacement of the spinal cord from the center of the CSF space. The intradural sensory ($r^2$<0.42, p>0.18) and discomfort ($r^2$<0.43, p>0.19) thresholds and the extradural discomfort thresholds ($r^2$<0.56, p>0.14) showed much weaker correlations with differences in the patient geometries.

Figure 13:
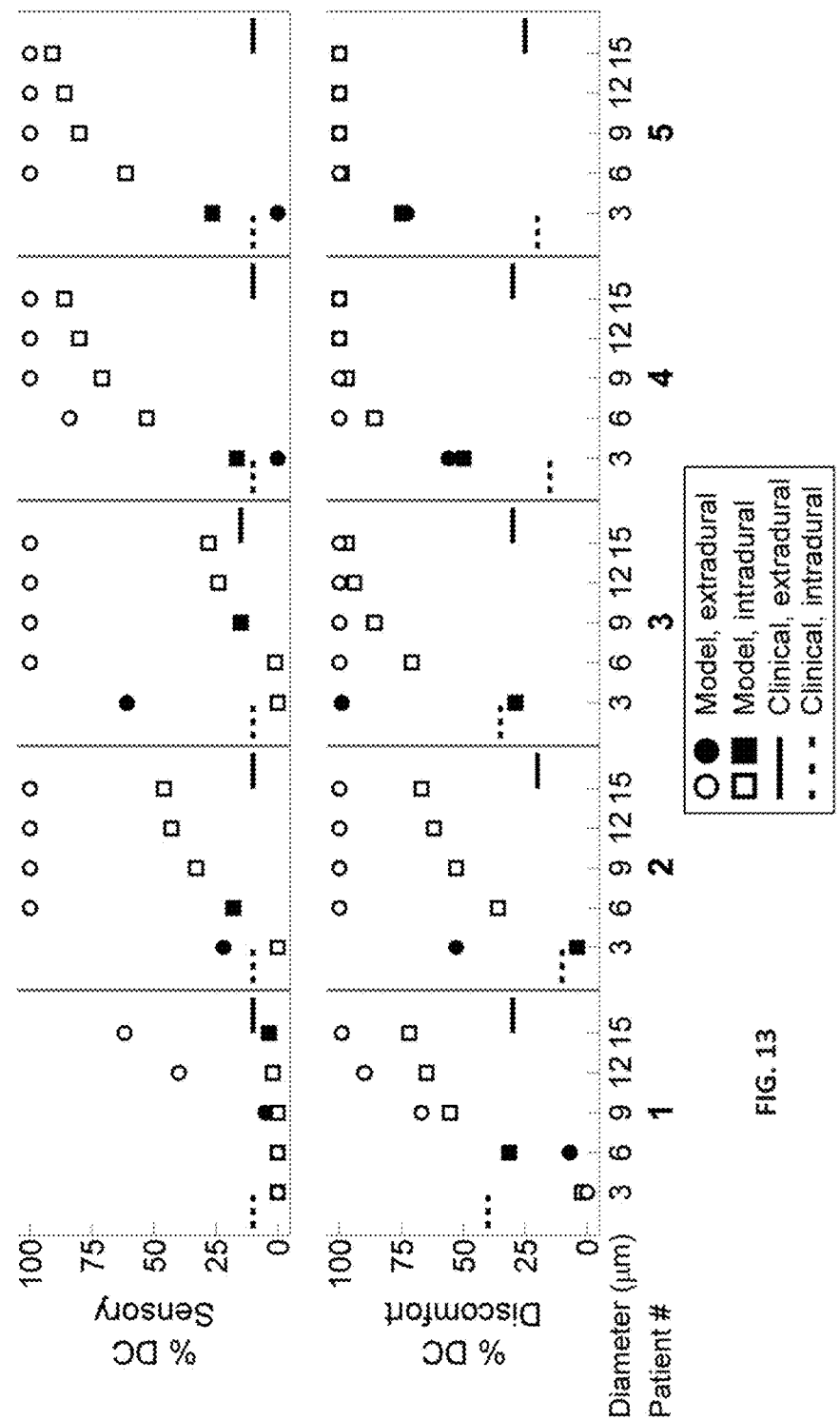
FIG. 13 are plots showing prediction of the diameter of dorsal column (DC) fibers activated based on clinical thresholds.

The number of dermatomes reported by patients at the sensory and discomfort thresholds was used to determine the diameter of the MRG model of DC fibers that most closely matched the clinical findings. The diameter of the model DC fiber population that most closely matched the sensory thresholds differed across patients and between the intradural and extradural cases in some of the patients, and the same was true for the diameters that most closely matched the discomfort thresholds (FIG. 13). Patients 2 and 3 reported paresthesia in T8 at their sensory thresholds, but because this was not consistent across patients in the intradural and extradural cases, the percentage and diameter of DR fibers to the sensory thresholds were not compared.

FIG. 13 illustrates plots showing prediction of the diameter of dorsal column (DC) fibers activated based on clinical thresholds. The percentage of MRG model DC fibers (denoted by circles and squares) activated at the sensory (top) and discomfort (bottom) thresholds compared to the percent activation expected (denoted by solid and dashed lines) based on the number of dermatomes reported at the corresponding clinical thresholds (see Methods). The filled shapes indicate the fiber diameters that yielded the smallest percent difference between the former and latter cases.

At the discomfort threshold in Patients 1-5, the locations of the paresthesias ranged from T8-S5 (FIG. 12), it was determined whether an increase in the activation of DC fibers or activation of DR fibers could predict discomfort. For all diameters except 3 μm (p=0.03), the distributions of the percentage of DC fiber activated at the discomfort and sensory thresholds across patients were not significantly different, and for all fiber diameters, there was no significant difference between the distributions of the percentage of DC and DR fibers activated at the discomfort thresholds.

In addition to the above, a comparison was made of the stimulation thresholds of SW models of DC fibers to the clinical stimulation thresholds. With the SW model, the diameter of the DC fiber population that most closely matched the sensory threshold was different across patients and between the intradural and extradural cases in some of the patients. In general, the stimulation thresholds predicted by the SW model were greater than the stimulation thresholds predicted by the MRG model, so compared to the MRG model, the SW model predicted that DC fibers with larger diameters were activated (FIG. 14).

Figure 14:
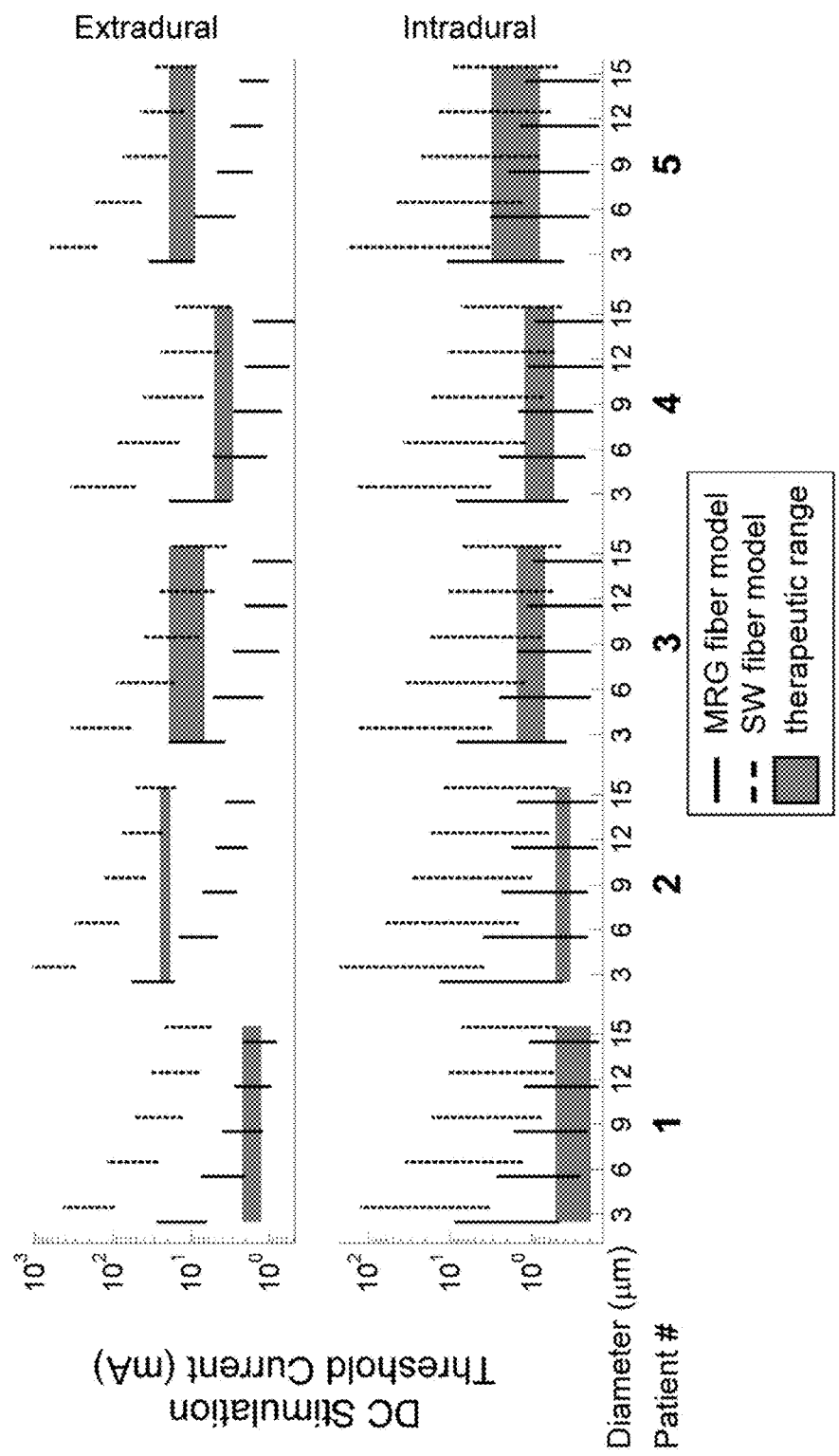
FIG. 14 are plots showing a comparison of model predictions of stimulation thresholds between the McIntyre, Richardson, Grill (MRG) and Sweeney (SW) models of dorsal column (DC) fibers.

FIG. 14 illustrates plots showing a comparison of model predictions of stimulation thresholds between MRG and SW models of dorsal column (DC) fibers. Plotted are distributions of the stimulation threshold currents of DC fibers when the AD-TECH was placed 1 mm above the spinal cord and 1 mm above the dura in the intradural and extradural cases, respectively. The therapeutic range is defined as the stimulation amplitudes between the measured sensory and discomfort thresholds.

Because fibers with diameters from 3-15 μm could be activated within the range of the two clinical thresholds, we used the intermediate fiber diameter, 9 μm, to quantify the efficiency and selectivity of SCS. The MRG model in the analyses described herein below.

For electrodes positioned along the midline, the calculated access resistance ($R_a$) of the AD-TECH array was 1,150Ω (mean, n=5) 1 mm above the dura mater, 165 Ω 1 mm below the dura mater, and 153 Ω 1 mm above the spinal cord. At a given dorsal-ventral position, distributions of $R_a$ across models of individual patients for electrodes at the three lateral deviations from the midline (0°, -10°, and -20°) were not significantly different from each other, but at a given lateral deviation, distributions of $R_a$ across models of individual patients were significantly different (p<0.05) between the dorsal-ventral positions. Therefore, $R_a$ was sensitive to dorsal-ventral position, primarily between the intradural and extradural locations, and insensitive to lateral deviations.

Figure 15:
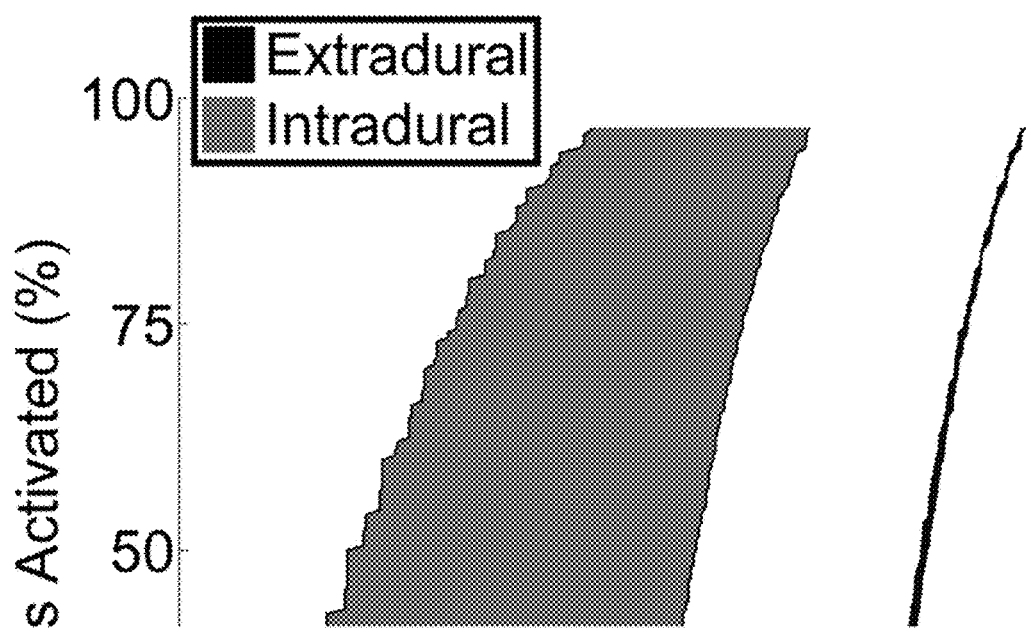
FIG. 15 is a graph showing power efficiency of extradural SCS versus intradural SCS.

The reduction of $R_a$ by >85% when the electrode was moved from the extradural space to the intradural space, along with the increased proximity of the electrode to the spinal cord, dramatically reduced the power required to activate DC fibers (FIG. 15). The average power required to activate half of the DC fibers at all six intradural locations was reduced >90% compared to epidural SCS at all three electrode locations.

FIG. 15 shows a graph showing power efficiency of extradural SCS versus intradural SCS. Average power required to stimulate the dorsal column (DC) fibers in the SCS model of Patient 2. The shaded black and grey areas encompass the range of stimulation powers calculated over the three extradural electrode locations and six intradural electrode locations, respectively.

The ability to activate selectively DC fibers over DR fibers was sensitive to electrode placement. In both the extradural and intradural cases, distributions of neural-element selectivity (i.e., $DC_0$) across models of individual patients at 0°, −10°, and −20° from the midline were significantly different (p<0.05) from each other. $DC_0$ was greatest when the lead was positioned along the midline and declined with increasing displacement of the electrode from the midline ((a) of FIG. 16). At each of the lateral displacements from the midline, the distribution of $DC_0$ across models of individual patients was significantly greater (p<0.05) with intradural placement than extradural placement. Thus, $DC_0$ was greatest when the intradural electrode was located along the midline and closest to the spinal cord.

Figure 16:
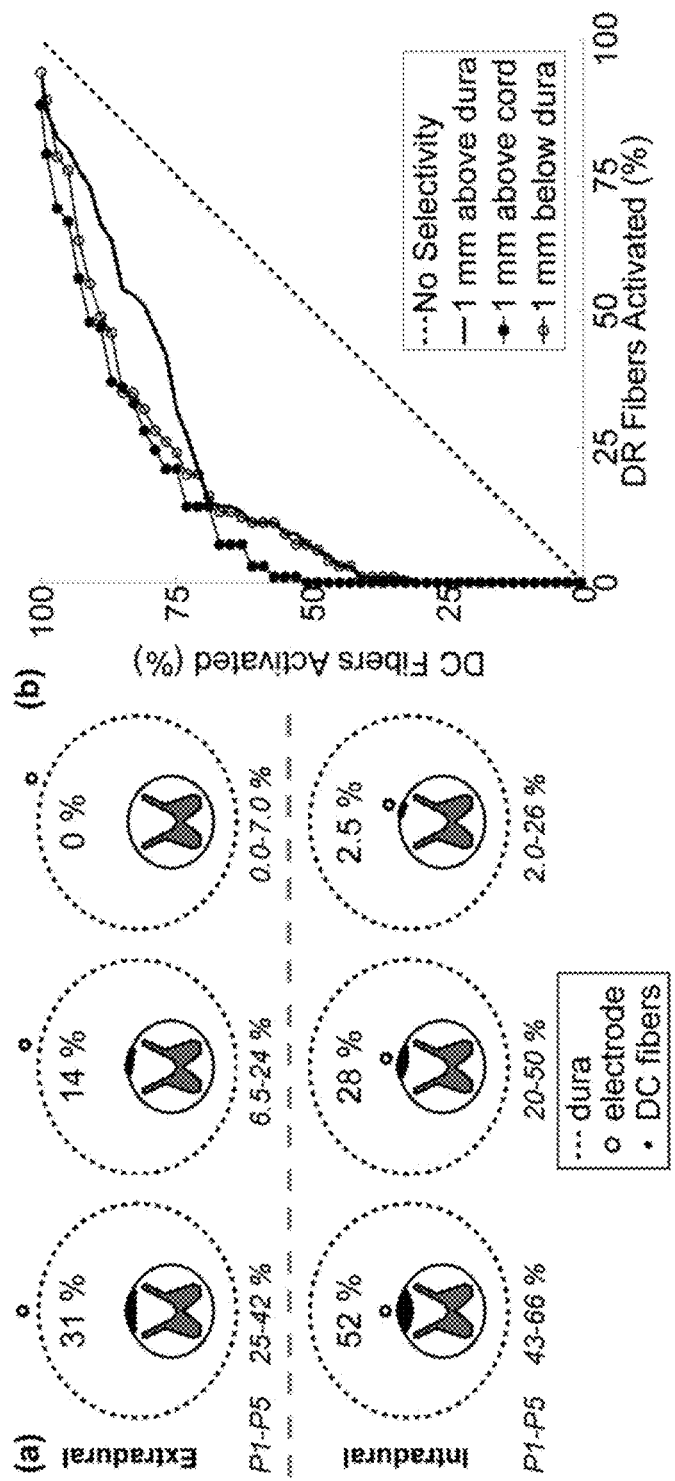
FIG. 16 illustrates a diagram and graph showing selectivity of extradural SCS versus intradural SCS in model of Patient 5.

FIG. 16 illustrates a diagram and graph showing selectivity of extradural SCS versus intradural SCS in model of Patient 5. The maximum percentage of dorsal column (DC) fibers activated with no activation of dorsal root (DR) fibers ($DC_0$) when the array was placed in the extradural (top row) and intradural (bottom row) spaces at lateral deviations of 0° (left column), −10° (middle column), and −20° (right column). For comparison, the range of $DC_0$ across all patients is shown below each panel. (b) of FIG. 16 shows curves of the proportion of DC fibers activated versus proportion of DR fibers activated for three different electrode locations along the midline.

It is not known how many DR fibers must be activated to evoke discomfort in SCS and whether this number varies from patient to patient. To account for this uncertainty in what constitutes discomfort, curves of the proportion of DR fibers activated versus proportions of the DC fibers activated (i.e., $DC_X$) were constructed. $DC_X$ was greater with intradural placement than with extradural placement when the electrode was located along the midline and closest to the spinal cord ((b) of FIG. 16).

Activation of DC fibers in lateral dermatomes at lower amplitudes than required for activation of DC fibers in medial dermatomes was possible by displacing the electrode laterally from the midline. For example, in Patient 1, when the array was positioned along the midline, 1 mm above the cord, DC fibers in L2-L5 could not be activated without first activating DC fibers in S2-S5 ((a) of FIG. 19). However, when the array was displaced −20° from the midline, 1 mm above the cord, DC fibers in L2-L5 may be activated but not without co-activation of DC fibers in S1 and S2 ((a) of FIG. 19). Similar results were obtained in Patients 2-5.

Figure 17:
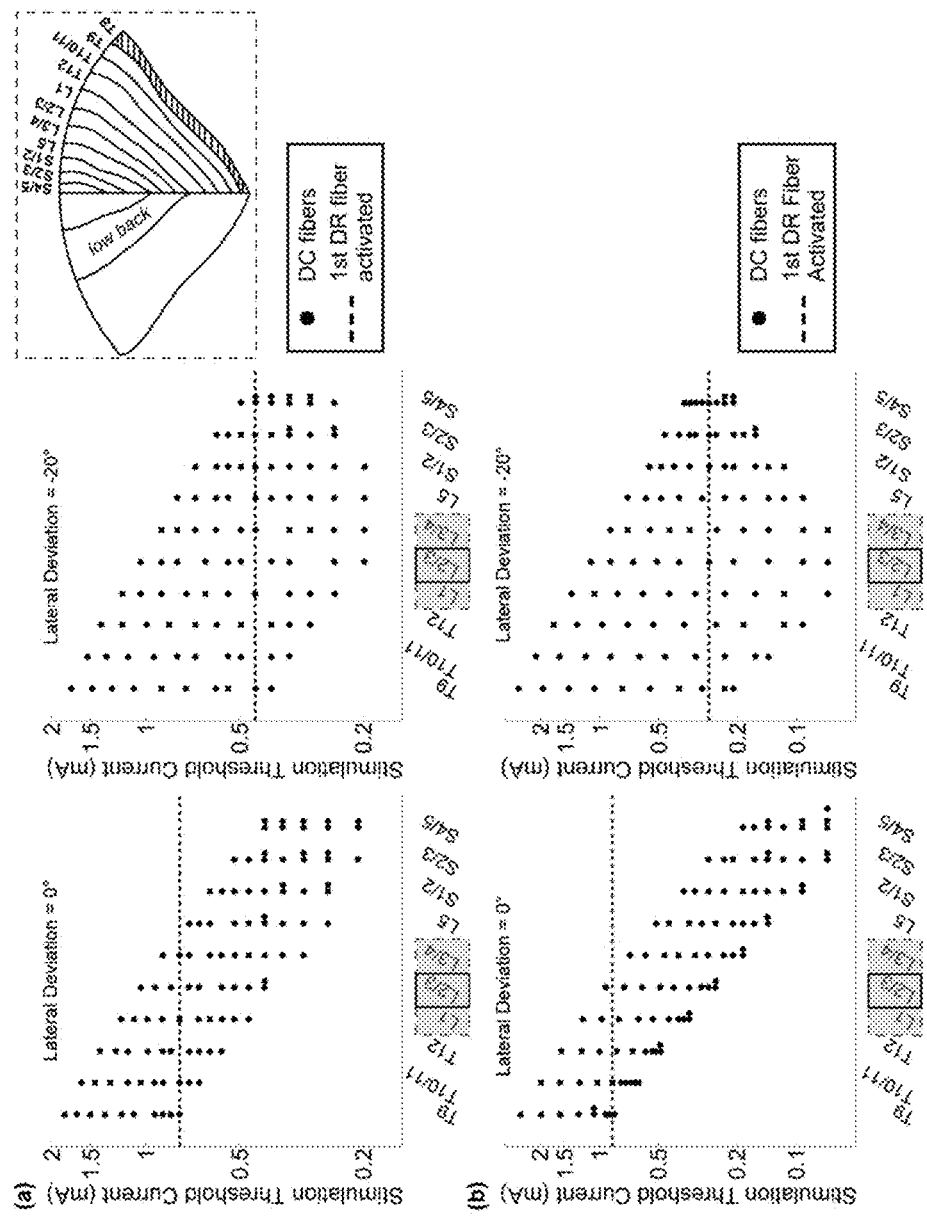
FIG. 17 are plots of selective activation of DC fibers in the low back (L2-L5) dermatomes of Patient 1.

FIG. 17 illustrates plots of selective activation of DC fibers in the low back (L2-L5) dermatomes of Patient 1. (a) of FIG. 17 shows stimulation threshold current of each of the model DC fibers, split by dermatome (see inset), when the AD-TECH array was placed in the intradural space and laterally displaced 0° (left) and −20° (right) from the midline. The shaded area in the inset illustrates where the Aβ collaterals of the DR fibers were located with respect to DC dermatomes at T8. The plots of (b) are the same as (a), except for the angular tripole electrode geometry. The locations of the paresthesias at the sensory and discomfort thresholds are denoted by the open black rectangles and filled grey rectangles, respectively.

The performance of five additional tripolar electrode designs (2 LT, 2 TT, and the AT) was tested in the SCS models of Patients 1-5. In the extradural case, LT-1.5, LT-6, TT-1, TT-3, and AT had an average (n=5) $DC_0$ of 30%, 31%, 27%, 19%, and 27%, respectively. However, the variability in $DC_0$ across patients was large. For example, LT-6, which performed the best, on average, had $DC_0$ that ranged from 23-38%; whereas TT-3, which performed the worst, on average, had $DC_0$ that ranged from 0-30% ((a) of FIG. 18). As a result, the distributions of the selectivities of the five designs were not significantly different from each other in the extradural case.

Figure 18:
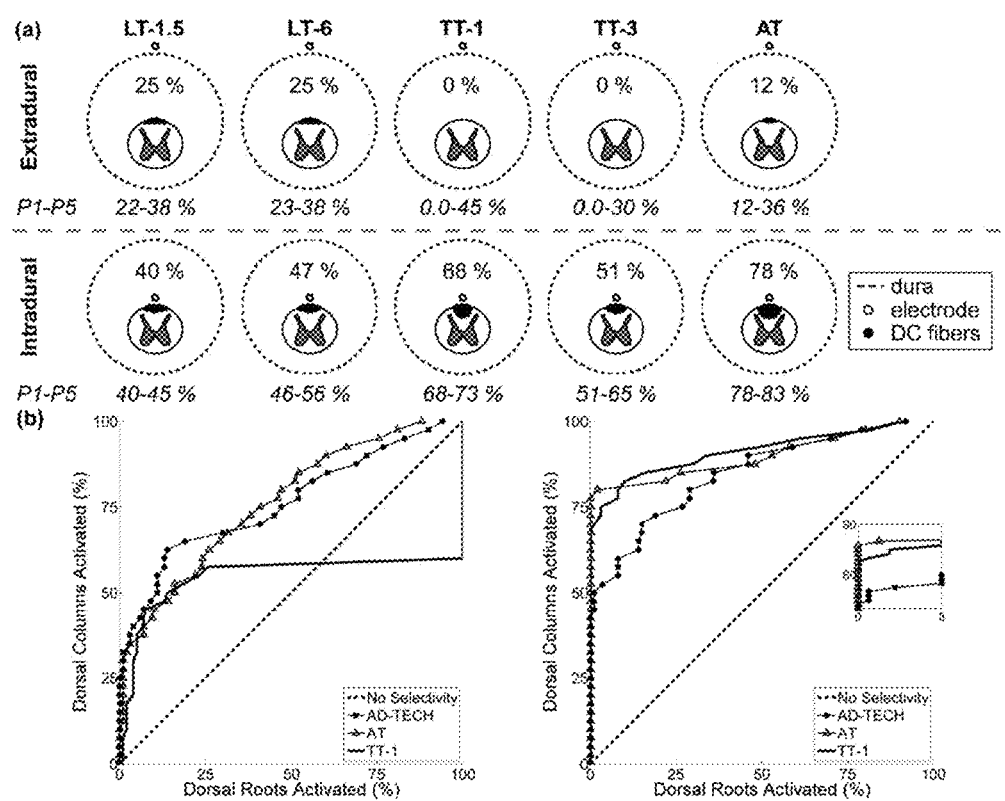
FIG. 18 are diagrams and graphs showing selectivity of five tripolar electrode designs in model of Patient 2.

All tripolar electrode designs had distributions of $DC_0$ in the intradural case that were significantly greater (p<0.01) than the corresponding distributions of $DC_0$ in the extradural case ((a) of FIG. 18). Further, in the intradural case, distributions of $DC_0$ of the electrode designs across models of individual patients were all significantly different from each other: the AT performed better than the two TTs (p<0.01), and the two TTs performed better than the two LTs (p<0.05). Thus, selectivity in the intradural case, compared to the extradural case, was less sensitive to anatomical variations across patients.

Since the AT had the greatest neural-element selectivity in the intradural case, we also assessed its ability to activate selectively DC fibers in the lateral dermatomes. When the AT was deviated −10° from the midline, it activated DC fibers in four dermatomes, L2-S2, without activation of DC fibers in the other dermatomes; and when further deviated to −20°, the AT activated DC fibers in three dermatomes, L1-L4, without activating DC fibers in the other dermatomes. In SCS for the treatment of chronic low back pain, the target dermatomes are typically L2-L5, thus the AT had the greatest selectivity in targeting the low back dermatomes ((b) of FIG. 18).

FIG. 18 illustrates diagrams and graphs showing selectivity of five tripolar electrode designs in model of Patient 2. (a) of FIG. 18 shows the percent of dorsal column (DC) fibers activated with no dorsal root (DR) fiber activation (i.e., $DC_0$) when the electrode was placed along the midline, 1 mm above (top) and below (bottom) the spinal cord. $DC_0$ is shown above the spinal cord. For comparison, the range of $DC_0$ across all patients is shown below each panel. (b) of FIG. 18 shows the proportion of DC fibers activated versus proportions of the DR fibers activated (i.e., $DC_X$) for three electrode designs in the extradural (left) and intradural (right) cases. The inset shows a close-up of the curves. LT=longitudinal tripolar, TT=transverse tripolar, AT=angular tripolar, and the number after the hyphen indicates the interelectrode spacing in mm.

A computational model of SCS was developed, and the efficiency and selectivity of different electrode designs placed either extradurally or intradurally were quantified. Intradural placement dramatically increased stimulation efficiency and reduced the power required to stimulate the dorsal columns by more than 90%. Intradural placement also enabled activation of a greater proportion of dorsal column fibers before spread of activation to dorsal roots and produced more selective activation of individual dermatomes at different lateral positions. Electrode designs used for extradural SCS are not optimal for intradural SCS, and a novel azimuthal tripolar design increased stimulation selectivity, even beyond that achieved with an intradural paddle array in TT configurations. Increased stimulation power efficiency is expected to increase the battery lives of implantable pulse generators (IPGs), increase the recharge intervals of rechargeable IPGs, and potentially reduce IPG volume. The greater stimulation selectivity with intradural placement may improve the success rate of SCS by mitigating the sensitivity of pain relief to malpositioning of the electrode.

Models incorporating patient-specific dimensions predicted the relative order of stimulation thresholds, the greater than five-fold difference between extradural and intradural stimulation thresholds, and the sensitivity of stimulation thresholds to spinal cord position (FIG. 14). However, across these five models, there was no clear distinction of either the diameter or proportion of Aβ fiber activation that correlated best with the sensory and discomfort thresholds of the patients (FIG. 13).

Myelinated fibers in the gracilis fasciculus and cuneatus fasciculus at T3 have diameters ranging from 1-15 μm, with ~60% between 1 and 3 μm; and myelinated fibers in the gracilis fasciculus at T5 have diameters ranging from 1-7 μm, with the majority between 2 and 3 μm. Prior models of extradural SCS showed that DC fibers with diameters >9.4 μm were activated between measured sensory and discomfort thresholds, and activation of large DC fibers with a diameter of 12 μm, which constitute <0.5% of all DC fibers, best matched measured sensory thresholds. The results of our study corroborated these prior findings in some patients (e.g., Patient 1), depending on the choice of axon model, but in the other patients (e.g., Patient 5), the results suggest that DC fibers with diameters as small as 3 μm are also activated at the sensory threshold (FIGS. 13 and 14).

The discrepancy between our results and previous findings may be explained by the choice of axon model. Prior models of extradural SCS used a simplified SW model of a mammalian nerve fiber with perfectly insulating myelin, whereas we used a more detailed MRG axon model that better replicates the excitability of mammalian nerve fibers. The SW model overestimated stimulation thresholds compared to the MRG model (FIG. 14), possibly explaining why prior modeling studies concluded that DC fibers with diameters >9 μm are the therapeutic targets of SCS.

The present results provide an alternate interpretation of which DC fibers are the potential therapeutic targets of SCS. Although it is possible that activation of one (or a few) 12 μm DC fibers is sufficient to evoke paresthesia, the results suggest that paresthesia induction requires activation of a larger proportion of DC fibers with diameters as small as 3 μm. Resolving these two possible interpretations may require more closely matching patient-specific models with the experimental conditions. For example, the presence of interstitial fluid and blood around the electrode and the distance and orientation of the stimulating array with respect to spinal cord will influence thresholds, and thereby influence the assessment of which Aβ fiber diameters are activated at sensory and discomfort thresholds. In addition, patient-to-patient variability in sensorimotor and pain networks (i.e., variability in the reporter) could influence threshold sensations.

Additionally, the clinical results provide an alternate interpretation of which neural elements are responsible for discomfort. Due to the relatively low stimulation thresholds of fibers entering the DR, discomfort is often associated with segmental motor reflexes and/or uncomfortable sensations that arise from stimulation of Ia and Aβ fibers in the DR, respectively. In our study, only Patients 3 and 5 reported discomfort in T8 (FIG. 12). Although the results cannot address where discomfort occurred or what were the qualities of discomfort, they provide evidence that discomfort can be associated with activation of Aβ fibers in both target and non-target dermatomes (FIG. 12). Further, a percent increase in activation of model DC fibers was not able to explain the onset of discomfort, so other mechanisms may be required to explain discomfort. For example, discomfort may arise from stimulation of other neural elements in the DC, such as ascending nociceptive fibers or descending fibers from the brain, or supra-threshold depolarization of Aβ fibers, which can result in a volley of action potentials per stimulation pulse, rather than a single action potential.

Previous studies of extradural SCS have shown that bipolar and tripolar electrode configurations have greater selectivity than monopolar configurations, but the energy required for stimulation increases as the IES decreases. More specifically, models of extradural SCS predict that PERC designs in longitudinal (rostrocaudal) bipolar (LB) and LT configurations have better selectivity than LAM designs in TT configurations, although the opposite is observed in practice. LAM designs are less prone to migration than PERC designs, and they compress the dural sac, reducing the distance between the electrodes and the spinal cord, which improves selectivity.

Results disclosed herein corroborate the predictions of previous extradural SCS studies. LT-1.5, LT-6, and the AD-TECH array in a LB configuration, on average, achieved greater $DC_0$ than TT-1 and TT-3 ((a) of FIG. 16 and (a) of FIG. 18); and energy requirements increased with decreasing IES. However, the distributions of the extradural $DC_0$ of the six electrode designs across patients were not significantly different from each other, indicating that patient-to-patient variability in spinal anatomy can significantly impact the performance of the electrode. In the intradural case, the relationship between energy requirements and IES did not change, but each design had greater selectivity than the corresponding extradural case ((a) of FIG. 16 and (a) of FIG. 18). Therefore, not only is selectivity increased with increasing proximity to the dorsal aspect of the spinal cord, but selectivity with intradural placement is less sensitive to patient anatomical variations.

The AT electrode design had the greatest selectivity in the intradural case (FIG. 18). To understand why the AT performed best, the centered second difference of the extracellular potentials ($\delta^2\Phi$) across the model fibers was examined for each electrode design, as $\delta^2\Phi$ is proportional to the source driving membrane polarization. Across all six designs, $\delta^2\Phi$ across DC fibers had the same stereotypical triphasic shape, including a primary positive (depolarizing) lobe flanked by two smaller negative (hyperpolarizing) lobes ((a) of FIG. 19). All six designs also generated a triphasic $\delta^2\Phi$ across DR fibers, except at the boundary between the CSF and the white matter, where the discontinuity in conductivity created discontinuity in $\delta^2\Phi$ ((a) of FIG. 19), which was expected. Since no marked differences in the shape of $\delta^2\Phi$ between the designs were observed, it was concluded that the superior selectivity of the AT arose from its ability to steer current away from the spinal cord so that $\delta^2\Phi$ decayed more rapidly with distance than it did with the LB, LT, and TT configurations. In other words, the difference in $\delta^2\Phi$ between the DC and DR fibers was greatest with the AT electrode ((b) of FIG. 19).

Figure 19:
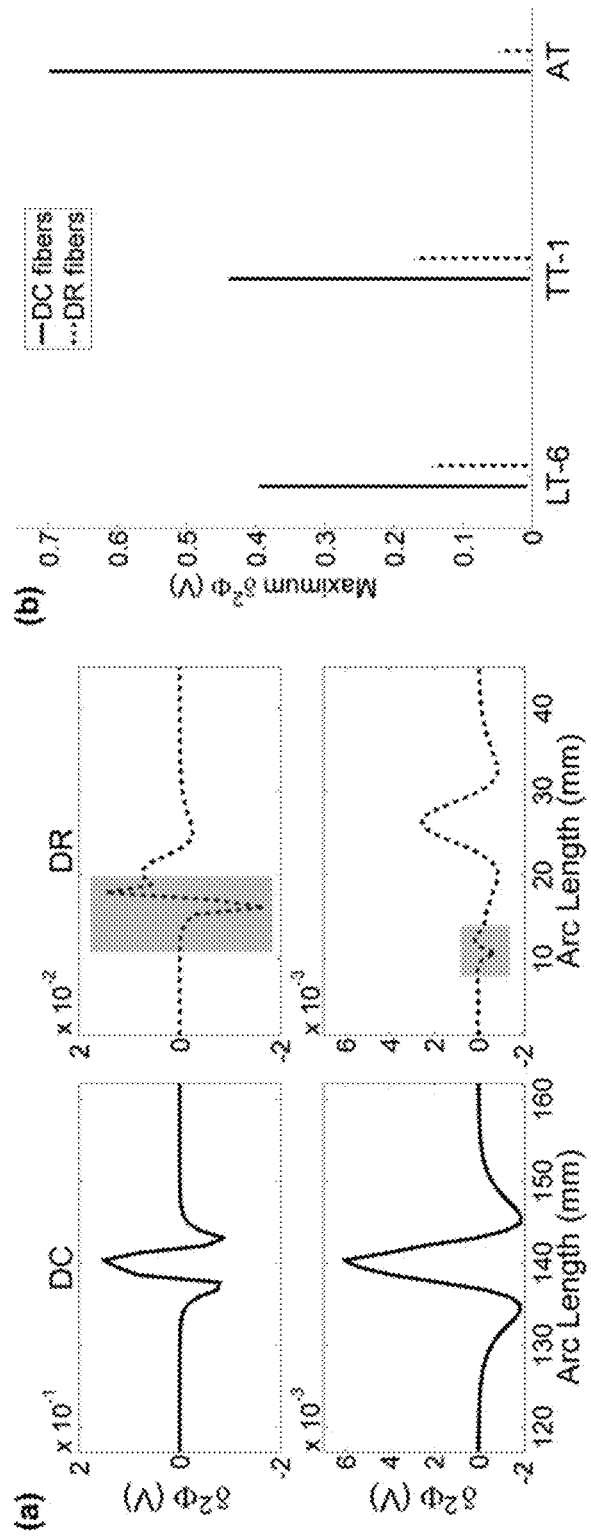
FIG. 19 illustrates graphs showing the source driving membrane polarization with three different electrode designs.

FIG. 19 illustrates graphs showing the source driving membrane polarization with three different electrode designs. (a) of FIG. 10 shows examples of the centered second difference of the potentials ($\delta^2\Phi$) along two DC fibers and two DR fibers. The grey boxes indicate regions where changes in tissue conductivity caused abrupt changes in $\delta^2\Phi$. (b) of FIG. 19 shows the range of maximum $\delta^2\Phi$ across all modeled DC fibers and DR fibers for three electrode configurations. LT=longitudinal tripolar, TT=transverse tripolar, AT=angular tripolar, and the number after the hyphen indicates the interelectrode spacing in mm.

In addition to efficiency and selectivity, additional factors, such as risk and cost, should also be considered when comparing the performance of PERC and LAM designs. PERC arrays are less invasive than LAM arrays: the former are inserted using a percutaneous needle, while the latter require multi-level laminectomies for placement. Further, compared to LAM arrays, PERC arrays are less prone to fracture and may be less damaging, as the tissue response depends on electrode size. In regards to practical limitations, PERC arrays are more prone to migration and movement than LAM arrays. For example, rotating the AT by $\pm 10°$, $\pm 20°$, and $\pm 30°$ about its longitudinal axis reduced the $DC_0$ from 80% to 73%, 58%, and 47.5%, respectively. Reductions in pain relief that result from lead migration or movement are problematic because they may lead to greater reoperation rates to replace or reposition the lead [30]. Despite these differences, the long-term health-care costs were similar between the PERC and LAM arrays [30].

It is noted that the branching collaterals of the A$\beta$ (DC) fibers were ignored. As the A$\beta$ fibers ascend the spinal cord to the *gracile* and *cuneate* nuclei in the brainstem, they project smaller diameter collaterals to neurons within the grey matter of the spinal cord. This branching can reduce stimulation thresholds by up to 50% in SW models of DC fibers, and the stimulation thresholds reported in the present study may therefore be overestimated.

It is also noted that the presence and properties of the electrode-tissue interface (ETI) were ignored. The filtering effects of the ETI have not been studied in SCS, but they have been studied in electrical stimulation of the brain. The ETI, which is typically modeled as the parallel combination of a distributed resistor and a distributed capacitor, has a time constant on the order milliseconds. Because typical pulse widths for SCS range from 175-600 µs, the ETI is expected to charge by an appreciable amount during the stimulus pulse, increasing the dynamic load on the stimulator. The rate at which the dynamic load increases depends on the electrical properties of the ETI and tissue, which depend on electrode geometry. Thus, representation of the ETI is recommended for future studies comparing the efficiency of SCS electrode designs.

The study described herein used a computational model of SCS to evaluate quantitatively the performance of intradural SCS for treating chronic pain. Intradural electrode placement markedly reduced energy consumption and improved selectivity of activation of DC fibers in both medial and lateral dermatomes without co-activation of DR fibers. Further, the results suggest that DC fibers with diameters as small as 3 µm are activated within the therapeutic range of SCS parameters, challenging the notion that only DC fibers with diameters >9 µm are activated in SCS. More anatomical studies are needed to characterize better the distribution of fiber diameters within the DC so that subsequent modeling studies can more accurately quantify the population of A$\beta$ fibers that correspond to evoking paresthesia and discomfort; and long-term clinical studies are needed to test the predications of our model, understand better the percentage and diameter of neural elements that correspond to comfortable and uncomfortable sensations, and assess the potential therapeutic benefits of intradural SCS The present disclosure may be a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

One skilled in the art will readily appreciate that the present subject matter is well adapted to carry out the objects and obtain the ends and advantages mentioned, as well as those inherent therein. The present examples along with the methods described herein are presently representative of various embodiments, are exemplary, and are not intended as limitations on the scope of the present subject matter. Changes therein and other uses will occur to those skilled in the art which are encompassed within the spirit of the present subject matter as defined by the scope of the claims.

What is claimed is:

1. A method comprising:
at least one processor and memory for:
providing an electroanatomical model of a patient spine and spinal cord including a map of target neural elements and non-target neural elements;
using model electrodes to simulate electrical stimulation of the target and non-target neural elements;
determining differences in activation thresholds between the target neural elements and the non-target neural elements in a plurality of different configurations of the model electrodes;
generating an optimal spinal cord stimulation electrode configuration based on the determined differences in activation thresholds; and
providing a spinal cord stimulation (SCS) device including electrodes based on the optimal spinal cord stimulation electrode configuration.

2. The method of claim 1, wherein the target neural elements are dorsal column fibers, and the non-target neural elements are dorsal root fibers.

3. The method of claim 1, wherein using model electrodes comprises applying a model rectangular pulse to the electrodes.

4. The method of claim 1, wherein providing a patient electroanatomic model comprises:
capturing one of a magnetic resonance image or a computed tomography image of a spine, spinal cord, dorsal columns, and dorsal roots of the patient; and
constructing the map based on the one of a magnetic resonance image or a computed tomography image.

5. The method of claim 1, wherein the electrodes of the SCS device correspond to the optimal spinal cord stimulation electrode configuration.

6. The method of claim 1, further comprising:
implanting the SCS device in the patient;
acquiring images of the SCS device and surrounding tissue to assess the location of and tissue response to presence and operation of the SCS device; and
generating another spinal cord stimulation electrode configuration based on the device location and the tissue response.

7. A method comprising:
at least one processor and memory for:
providing an electroanatomical model of a patient spine and spinal cord including a map of target neural elements and non-target neural elements;
using model electrodes to simulate electrical stimulation of the target and non-target neural elements;
determining differences in activation thresholds between the target neural elements and the non-target neural elements in a plurality of different configurations of the model electrodes; and
generating an optimal spinal cord stimulation electrode configuration based on the determined differences in activation thresholds, and
wherein generating an optimal spinal cord stimulation electrode configuration comprises optimizing electrode geometry and spacing in a spinal cord stimulation (SCS) device based on the determined differences in activation thresholds.

8. The method of claim 7, further comprising determining stimulation parameters for the electrodes based on the determined differences in activation thresholds.

9. The method of claim 7, wherein the SCS device has one of a longitudinal bipolar and tripolar configuration.

10. The method of claim 1, further comprising:
constructing a curve, p(x), of the proportion of the non-target neural elements activated versus selected proportions of the target neural elements;
calculating the area under the curve;
quantifying stimulation efficiency by calculating electrical energy consumed by a stimulation pulse activating the target neural elements;
determining a cost function of different configurations of the model electrodes based on the calculated area under the curve and the stimulation efficiency.

11. The method of claim 10, wherein quantifying stimulation efficiency comprises applying the following equation to calculate electrical energy:

$$E=\int I(t)V(t)dt,$$

wherein I and V are the applied stimulation voltage and current, respectively.

12. The method of claim 1, wherein generating an optimal spinal cord stimulation electrode configuration comprising selecting one or more of a contact number, a contact polarity, and an electrode position for the model electrodes.

13. The method of claim 12, wherein selecting comprises selecting the one or more of a contact number, a contact polarity, and an electrode position for the model electrodes to utilize minimal energy to activate target neural elements with minimal co-activation of non-target neural elements.

14. The method of claim 12, wherein selecting comprises selecting the one or more of a contact number, a contact polarity, and an electrode position for the model electrodes to minimize a cost function defined by a linear or non-linear combination of weighted measures of selectivity and efficiency.

15. A system of providing a spinal cord stimulation (SCS) device, the system comprising:
at least one processor and memory configured to:
provide an electroanatomical model of a patient spine and spinal cord including a map of target neural elements and non-target neural elements;
use model electrodes to simulate electrical stimulation of the target and non-target neural elements;
determine differences in activation thresholds between the target neural elements and the non-target neural elements in a plurality of different configurations of the model electrodes; and
generate an optimal spinal cord stimulation electrode configuration based on the determined differences in activation thresholds; and
a spinal cord stimulation (SCS) device including electrodes positioned based on the optimal spinal cord stimulation electrode configuration.

16. The system of claim 15, wherein the target neural elements are dorsal column fibers, and the non-target neural elements are dorsal root fibers.

17. The system of claim 15, wherein the at least one processor and memory is configured to apply a model rectangular pulse to the electrodes.

18. The system of claim 15, wherein the at least one processor and memory is configured to:
capture one of a magnetic resonance image or a computed tomography image of a spine, spinal cord, dorsal columns, and dorsal roots of the patient; and
construct the map based on the one of a magnetic resonance image or a computed tomography image.

19. The system of claim 15, the at least one processor and memory is configured to produce a spinal cord stimulation (SCS) device including electrodes based on the optimal spinal cord stimulation electrode configuration.

20. The system of claim 19, wherein the electrodes of the SCS device correspond to the optimal spinal cord stimulation electrode configuration.

21. The system of claim 19, wherein the at least one processor and memory is configured to:
acquire images of the SCS device while implemented in a patient and surrounding tissue to assess the location of and tissue response to operation of the SCS device; and
generate another spinal cord stimulation electrode configuration based on the device location and the tissue response.

22. The system of claim 15, wherein the at least one processor and memory is configured to optimize electrode geometry and spacing in a spinal cord stimulation (SCS) device based on the determined differences in activation thresholds.

23. The system of claim 22, wherein the at least one processor and memory is configured to determining stimulation parameters for the electrodes based on the determined differences in activation thresholds.

24. The system of claim 22, wherein the SCS device has one of a longitudinal bipolar and tripolar configuration.

25. The system of claim 15, wherein the at least one processor and memory is configured to:
construct a curve, p(x), of the proportion of the non-target neural elements activated versus selected proportions of the target neural elements;
calculate the area under the curve;
quantify stimulation efficiency by calculating electrical energy consumed by a stimulation pulse activating the target neural elements;
determine a cost function of different configurations of the model electrodes based on the calculated area under the curve and the stimulation efficiency.

26. The system of claim 25, wherein the at least one processor and memory is configured to apply the following equation to calculate electrical energy:

$$E=\int I(t)V(t)dt,$$

wherein I and V are the applied stimulation voltage and current, respectively.

27. The system of claim 15, wherein the at least one processor and memory is configured to select one or more of a contact number, a contact polarity, and an electrode position for the model electrodes.

28. The system of claim 27, wherein the at least one processor and memory is configured to select the one or more of a contact number, a contact polarity, and an electrode position for the model electrodes to utilize minimal energy to activate target neural elements with minimal co-activation of non-target neural elements.

29. The system of claim 15, wherein the at least one processor and memory is configured to select one or more of a contact number, a contact polarity, and an electrode position for the model electrodes so as to minimize a cost function defined by a linear or non-linear combination of weighted measures of selectivity and efficiency.

* * * * *